United States Patent [19]
Pearlman et al.

[11] Patent Number: 5,837,870
[45] Date of Patent: Nov. 17, 1998

[54] PROCESS TO PREPARE OXAZOLIDINONES

[75] Inventors: Bruce A. Pearlman; William R. Perrault; Michael R. Barbachyn, all of Kalamazoo; Peter R. Manninen, Portage; Dana S. Toops, Kalamazoo; David J. Houser, Portage; Thomas J. Fleck, Scotts, all of Mich.

[73] Assignee: Pharmacia & Upjohn Company, Kalamazoo, Mich.

[21] Appl. No.: 828,923

[22] Filed: Mar. 28, 1997

Related U.S. Application Data

[60] Provisional application No. 60/015,499 Apr. 11, 1996.
[51] Int. Cl.$^6$ .................. C07D 413/04; C07D 249/16
[52] U.S. Cl. .................. 544/137; 544/369; 548/217; 548/221; 548/229; 548/257
[58] Field of Search .................. 548/257, 217, 548/221, 229; 544/137, 369

[56] References Cited

U.S. PATENT DOCUMENTS

| | | | |
|---|---|---|---|
| 3,547,951 | 12/1970 | Hardie et al. | 260/340.9 |
| 4,062,862 | 12/1977 | Fujimoto et al. | 260/307 |
| 4,150,029 | 4/1979 | Dostert et al. | 260/307 |
| 4,236,012 | 11/1980 | Fujimoto et al. | 548/229 |
| 4,250,318 | 2/1981 | Dostert et al. | 548/229 |
| 4,340,606 | 7/1982 | Fugitt et al. | 424/272 |
| 4,461,773 | 7/1984 | Gregory | 424/272 |
| 4,476,136 | 10/1984 | Dostert et al. | 424/272 |
| 4,948,801 | 8/1990 | Carlson et al. | 514/307 |
| 5,164,510 | 11/1992 | Brickner | 548/231 |
| 5,182,403 | 1/1993 | Brickner | 548/231 |
| 5,210,303 | 5/1993 | Sugiyama | 564/407 |
| 5,225,565 | 7/1993 | Brickner | 548/229 |
| 5,231,188 | 7/1993 | Brickner | 548/221 |
| 5,247,090 | 9/1993 | Brickner | 546/89 |

FOREIGN PATENT DOCUMENTS

| | | | |
|---|---|---|---|
| 681830 | 3/1964 | Canada | 260/307.2 |
| WO93/09103 | 5/1993 | WIPO | C07D 263/20 |
| WO93/23384 | 11/1993 | WIPO | C07D 263/20 |
| WO95/07271 | 3/1995 | WIPO | C07D 263/20 |
| WO96/13502 | 5/1996 | WIPO | C07D 413/10 |
| WO96/15130 | 5/1996 | WIPO | C07D 491/048 |

OTHER PUBLICATIONS

*J. Med. Chem.,* 32, p. 1673 (1989).
*Tetrahedron,* 45, p. 1323 (1989).
*Abstracts of Papers,* 206th National Meeting of the American Chemical Society, Chicago IL, Aug., 1993. American Chemical Society: Washington, DC 1993; ORGN 089.
*J. Med. Chem.,* 39, 673 (1996).
*J. Med. Chem.,* 39, 680 (1996).
*Abstracts of Papers,* 35th Interscience Conference on Antimicrobial Agents and Chemotherapy, San Francisco, CA Sep., 1995; American Society for Microbiology; Washington, DC, 1995: Abstract No. F208, F207, F206, F227.
*J. Am. Chem. Soc.,* 64, p. 1291 (1942).
*Chem. Lett.,* p. 1057 (1978).

*Primary Examiner*—Johann Richter
*Assistant Examiner*—Ebenezer Sackey
*Attorney, Agent, or Firm*—Bruce Stein

[57] ABSTRACT

The present invention includes processes for producing 5-hydroxymethyl substituted oxazolidinone alcohols (III) from carbamates (IIA) or a trifluoroacetamide (IIB) using a dihydroxy compound (I) or glycidol (IV) starting material and for the transformation of the hydroxymethyl substituted oxazolidinone alcohols (III) to the corresponding amino compounds, 5-aminomethyl substituted oxazolidinone amines (VII) which are acylated to form commercially useful antibacterial 5-acylamidomethyl substituted oxazolidinone (VIII).

37 Claims, No Drawings

PROCESS TO PREPARE OXAZOLIDINONES

CROSS-REFERENCE TO RELATED APPLICATIONS

This application claims the benefit of U.S. provisional application Ser. No. 60/015,499 filed 11 Apr. 1996, under 35 USC §119(e)(i).

BACKGROUND OF THE INVENTION

1. Field of the Invention

The present invention relates to processes for producing 5-hydroxymethyl substituted oxazolidinone alcohols (III). Also disclosed is a process for transformation of the 5-hydroxymethyl substituted oxazolidinone alcohols (III) to the corresponding 5-aminomethyl substituted oxazolidinone amines (VII) which are useful in the production of oxazolidinone antibacterial pharmaceuticals (VIII).

2. Description of the Related Art

U.S. Pat. Nos. 5,164,510, 5,182,403 and 5,225,565 disclose 5'-indolinyloxazolidinones, 3-(5'-indazolyl) oxazolidinones, 3-(fused-ring substituted) phenyloxazolidinones respectively useful as antibacterial agents.

U.S. Pat. Nos. 5,231,188 and 5,247,090 disclose various tricyclic [6.5.5] and [6.6.5]-fused ring oxazolidinones useful as antibacterial agents.

International Publication W093/09103 discloses mono- and di-halo phenyl oxazolidinone anti-bacterials which are useful as pharmaceutical agents for their anti-bacterial action.

U.S. Pat. Nos. 4,150,029, 4,250,318, 4,476,136, 4,340,606 and 4,461,773 disclose the synthesis of 5-hydroxymethyloxazolidinones from amines (R-NHX$_1$, where X$_1$ is —H or p-toluenesulfonyl) and R,S-glycidol (C*H$_2$—O—C*H—CH$_2$—OH where the carbon atoms marked* are bonded together, cyclized to form an epoxide). The mixture of enantiomers produced by this process (represented by the formula R—NH—CH$_2$—CHOH—CH$_2$—OH) are separated by fractional crystallization of the mandelic acid salts. The enantiomerically pure R-diol is then converted into the corresponding 5R-hydroxymethyl substituted oxazolidinones (III) by condensation with diethylcarbonate in the presence of sodium methoxide. These 5R-hydroxymethyl substituted oxazolidinones are useful as synthetic precursors of pharmaceutically useful oxazolidinones. The large number of steps renders this process unattractive.

J. Med. Chem., 32, 1673 (1989), Tetrahedron 45, 1323 (1989) and U.S. Pat. No. 4,948,801 disclose a method of producing oxazolidinones which comprises reacting an isocyanate (R—N=C=O) with (R)-glycidyl butyrate in the presence of a catalytic amount of lithium bromide—tributylphosphine oxide complex to produce the corresponding 5R-butyryloxymethyl substituted oxazolidinone. The process is performed at 135°–145°. The butyrate ester is then hydrolyzed in a subsequent step to give the corresponding 5-hydroxymethyl substituted oxazolidinone. The relative high cost and/or availability of the isocyanate starting material and requirement of high temperature detract significantly from the attractiveness of this method.

Abstracts of Papers, 206th National Meeting of the American Chemical Society, Chicago, Ill. August, 1993; American Chemical Society: Washington, D.C., 1993; ORGN 089; J. Med. Chem. 39, 673 (1996); J. Med. Chem. 39, 680 (1996); International Publications W093/09103, W093/09103, W095/07271 and W093/23384; PCT applications PCT/US95/12751 and PCT/US95/10992; Abstracts of Papers, 35th Interscience Conference on Antimicrobial Agents and Chemotherapy, San Francisco, Calif. September, 1995; American Society for Microbiology: Washington, D.C. 1995; Abstract No. F208; Abstracts of Papers, 35th Interscience Conference on Antimicrobial Agents and Chemotherapy, San Francisco, Calif. September, 1995; American Society for Microbiology: Washington, D.C. 1995; Abstract No. F207; Abstracts of Papers, 35th Interscience Conference on Antimicrobial Agents and Chemotherapy, San Francisco, Calif. September, 1995; American Society for Microbiology: Washington, D.C. 1995; Abstract No. F206; Abstracts of Papers, 35th Interscience Conference on Antimicrobial Agents and Chemotherapy, San Francisco, Calif. September, 1995; American Society for Microbiology: Washington, D.C. 1995; Abstract No. F227; disclose the reaction of a carbamate with n-butyllithium, lithium diisopropylamide or lithium hexamethyldisilazide at −78° to −40° followed by glycidyl butyrate at −78° followed by warming to 20°–25° to produce 5-hydroxymethyl substituted oxazolidinones (III) where the ester is cleaved during the reaction.

U.S. Pat. Nos. 4,062,862 and 4,236,012 disclose a process to prepare oxazolidinones which comprises reacting an epoxide with a primary (lacking any substituent on the nitrogen atom) carbamate in the presence of a catalyst. The process "is preferably conducted at a temperature of from 100° to 150° for several hours."

Canadian Patent 681,830 discloses a process to prepare oxazolidinones which comprises reacting an aryl ether of glycidol with a primary carbamate in the presence of an alkaline catalyst (preferably lithium amide or lithium hydroxide). The process was performed in the "preferred temperature range of 150° to 165°". The products are aryl ethers of 5-hydroxymethyl substituted oxazolidinones and the yields are poor (40–78%).

J. Am Chem. Soc., 64, 1291 (1942) and U.S. Pat. No. 3,547,951 disclose a method for converting primary alcohols to amines that involves treatment with methane sulfonyl chloride to produce the mesylate followed by contacting the mesylate with anhydrous ammonia at ambient temperature in a sealed reaction vessel under high pressure.

It is also known that the mesylates of primary alcohols react with aqueous ammonia to give the corresponding primary amines, but high temperature and high pressure (85 psig) are required. Normally this process cannot be used in ordinary general purpose reactors and must be run in special reactors rated for high pressure.

International Publication W095/07271 discloses the ammonolysis of oxazolidinone mesylates.

U.S. Pat. No. 4,476,136 discloses a method of transforming 5-hydroxymethyl substituted oxazolidinones (III) to the corresponding 5(S)-aminomethyl substituted oxazolidinones (VII) that involves treatment with methane sulfonyl chloride followed by potassium phthalimide followed by hydrazine. This reaction sequence produces by-products which are difficult to separate from the desired product.

J. Med. Chem., 32, 1673 (1989) and Tetrahedron 45, 1323 (1989) disclose a method for transforming 5-hydroxymethylsubstituted oxazolidinones into the corresponding 5S-acetamidomethyl substituted oxazolidinones that involves treatment with methanesulfonyl chloride or tosyl chloride, followed by sodium azide, followed by trimethylphosphite or platinum dioxide/hydrogen, followed by acetic anhydride or acetyl chloride to give the desired 5(S)-acetamidomethyl substituted oxazolidinone. It is known that sodium azide is an explosion hazard.

U.S. Pat. 5,210,303 discloses the conversion of various substituted benzyl chlorides into the corresponding benzylamines by heating with aqueous ammonia in the presence of aromatic aldehydes to suppress dialkylation. The dialkylated impurity is generally difficult to remove, see Chem. Lett., 1057 (1978).

SUMMARY OF INVENTION

Disclosed is a process to prepare 5-hydroxymethyl substituted oxazolidinones of formula (III)

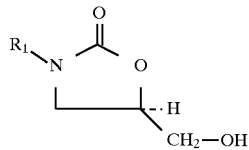

(III)

where $R_1$ is

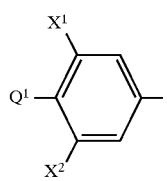

where $X^1$ is —H or —F;
where $X^2$ is —H or —F;
where $Q^1$ is:

a) 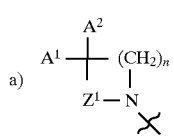

b) 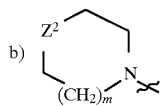

c) 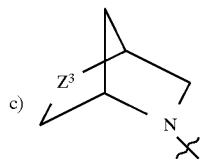

d) 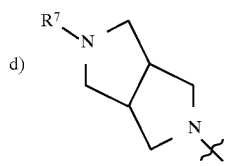

f) 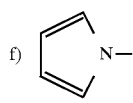

g) 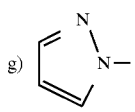

h) 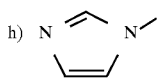

i) 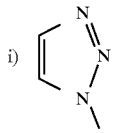

j) 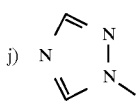

k) 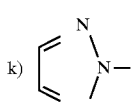

m) 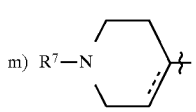

$Q^1$ and $X^2$ taken together are:

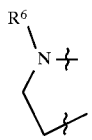

where $Z^1$ is:
  a) —CH$_2$—,
  b) —CH(R$^4$)—CH$_2$—,
  c) —C(O)—, or
  d) —CH$_2$CH$_2$CH$_2$—;
where $Z^2$ is:
  a) —O$_2$S—,
  b) —O—,
  c) —N(R$^7$)—,
  d) —OS—, or
  e) —S—;
where $Z^3$ is:
  a) —O$_2$S—,
  b) —O—,
  c) —OS—, or
  d) —S—;
where $A^1$ is:
  a) H—or
  b) CH$_3$;
where $A^2$ is:
  a) H—,
  b) HO—,
  c) CH$_3$—,
  d) CH$_3$O—,
  e) R$^2$O—CH$_2$—C(O)—NH—
  f) R$^3$O—C(O)—NH—,
  g) (C$_1$-C$_2$)alkyl- O—C(O)—,
  h) HO—CH$_2$—,
  i) CH$_3$O—NH—, j) $(C_1-C_3)$alkyl- $O_2C$—
k) $CH_3$—C(O)—,
l) $CH_3$—C(O)—$CH_2$—, m) 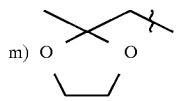

n) 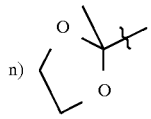

$A^1$ and $A^2$ taken together are:

a) 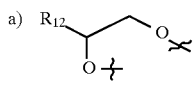

b) 

c) 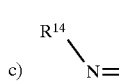

where $R^1$ is:
 a) —CHO,
 b) —$COCH_3$,
 c) —$COCHCl_2$,
 d) —$COCHF_2$,
 e) —$CO_2CH_3$,
 f) —$SO_2CH_3$, or
 g) —$COCH_2OH$;
where $R^2$ is:
 a) H—,
 b) $CH_3$—,
 c) phenyl-$CH_2$—, or
 d) $CH_3C(O)$—;
where $R^3$ is:
 a) $(C_1-C_3)$alkyl-, or
 b) phenyl-;
where $R^4$ is:
 a) H—, or
 b) HO—;
where $R^5$ is:
 a) H—,
 b) $(C_1-C_3)$alkyl-,
 c) $CH_2=CH-CH_2$— or
 d) $CH_3-O-(CH_2)_2-$;
where $R^6$ is:
 a) $CH_3$—C(O)—,
 b) H—C(O)—,
 c) $Cl_2CH$—C(O)—,
 d) $HOCH_2$—C(O)—,
 e) $CH_3SO_2$—, f) 

g) $F_2CHC(O)$—, h) 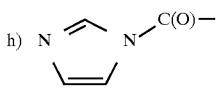

i) $H_3C$—C(O)—O—$CH_2$—C(O)—,
j) H—C(O)—O—$CH_2$—C(O)—, k) 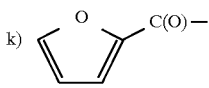

l) HC≡CH—$CH_2O$—$CH_2$—C(O)—or
m) phenyl-$CH_2$—O—$CH_2$—C(O)—;
where $R^7$ is:
 a) $R^2$—C($R^{10}$)($R^{11}$)—C(O)—,
 b) $R^3O$—C(O)—,
 c) $R^8$—C(O)—, d) 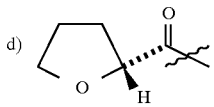

e) 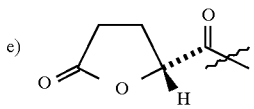

f) $H_3C$—C(O)—$(CH_2)_2$—C(O)—,
g) $R^9$—$SO_2$—, h) 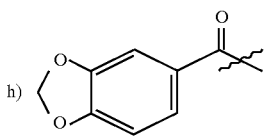

i) HO—$CH_2$—C(O)—,
j) $R^{16}$—$(CH_2)_2$—,
k) $R^{13}$—C(O)—O—$CH_2$—C(O)—,
l) $(CH_3)_2N$—$CH_2$—C(O)—NH—,
m) NC—$CH_2$—or
n) $F_2$—CH—$CH_2$—;
where $R^8$ is:
 a) H—,
 b) $(C_1-C_4)$alkyl,
 c) aryl —(CH2)p
 d) $ClH_2C$—,
 e) $Cl_2HC$—,
 f) $FH_2C$—,
 g) $F_2HC$—or
 h) $(C_3-C_6)$cycloalkyl;
where $R^9$ is:
 a) —$CH_3$,
 b) —$CH_2Cl$,
 c) —$CH_2CH=CH_2$,
 d) aryl or
 e) —$CH_2CN$;
where $R^{10}$ is H— or $CH_3$—;
where $R^{11}$ is H— or $CH_3$—;
where $R^{12}$ is:
 a) H—,
 b) $CH_3O$—$CH_2O$—$CH_2$— or c) HOCH$_2$—;

where R$^{13}$ is:
  a) CH$_3$—,
  b) HOCH$_2$—,
  c) (CH$_3$)$_2$N-phenyl, or
  d) (CH$_3$)$_2$N—CH$_2$—;

where R$^{14}$ is:
  a) HO—,
  b) CH$_3$O—,
  c) H$_2$N—,
  d) CH$_3$O—C(O)—,
  e) CH$_3$—C(O)—O—CH$_2$—C(O)—O—,
  f) phenyl-CH$_2$—O—CH$_2$—C(O)—O—,
  g) HO—(CH$_2$)$_2$—O—,
  h) CH$_3$O—CH$_2$—O—(CH$_2$)$_2$—O—, or
  i) CH$_3$O—CH$_2$O—;

where R$^{15}$ is:
  a) H— or
  b) Cl—;

where R$^{16}$ is:
  a) HO—
  b) CH$_3$O—, or
  c) F;

where m is 0 or 1;

where n is 1 thru 3;

where p is 0 or 1;

where aryl is phenyl substituted with zero (0) or one (1) of the following:
  a) —F,
  b) —Cl,
  c) —OCH$_3$,
  d) —OH,
  e) —NH$_2$,
  f) —(C$_1$-C$_4$)alkyl,
  g) —O—C(O)—OCH$_3$, or
  h) —NO$_2$ and protected forms thereof, which comprises contacting a hydroxy compound selected from the group consisting of:
    (a) (S)-, (R)-dihydroxy compound of formula (I)

M$_1$—CH$_2$—CH(OH)—CH$_2$—OH        (I)

or any mixture thereof where M$_1$ is —Cl, —Br or —O—SO$_2$—φ-CH$_3$, or (b) (S)-, (R)-glycidol (IV)

C*H$_2$—C*H—CH$_2$—OH        (IV)

or any mixture thereof where the carbon atoms designated by an * are each bonded to the same oxygen atom (—O—) to form a three member ring, with a carbamate of formula (IIA)

R$_1$—NH—CO—O—M$_2$        (IIA)

or a trifluoroacetamide of formula (IIB)

R$_1$—NH—CO—CF$_3$        (IIB)

in the presence of a lithium cation and a base whose conjugate acid has a pK$_a$ of greater than about 8 where —O—M$_2$ is a base whose acid has a pk$_a$ of between about 8 and about 24, and where R$_1$ is as defined above.

Also disclosed is a process to prepare 5-aminomethyl substituted oxazolidinone amines of formula (VII)

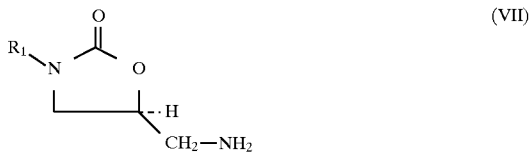
(VII)

where R$_1$ is as defined above, which comprises:
  (1) contacting 5-hydroxymethyl substituted oxazolidinone alcohols of formula (III)

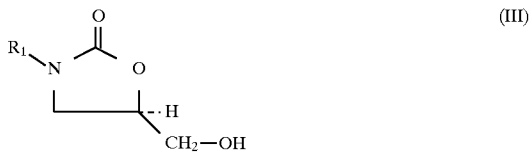
(III)

where R$_1$ is as defined above with a sulfonylating agent selected from the group consisting of compounds of formula (V$_a$-V$_d$)

M$_3$—SO$_2$—C$_6$H$_{n3}$(NO$_2$)$_{n1}$Cl$_{n2}$        (V$_a$)

O[—SO$_2$—C$_6$H$_{n3}$(NO$_2$)$_{n1}$Cl$_{n2}$]$_2$        (V$_b$)

O(SO$_2$—F)$_2$        (V$_c$)

O(SO$_2$—CF$_3$)$_2$        (V$_d$)

where n$_1$ is 0, 1 or 2;
where n$_2$ is 0 thru 4 with the provisos that:
  if n$_1$ is 0, n$_2$ is 2, 3 or 4,
  if n$_1$ is 1, n$_2$ is 0 or 1,
  if n$_1$ is 2, n$_2$ is 0;
where n$_3$ is 5-(n$_1$+n$_2$);
where M$_3$ is Cl— or Br— to produce the corresponding oxazolidinone sulfonate of formula (VI$_a$-VI$_d$)

(VIa or VIb)

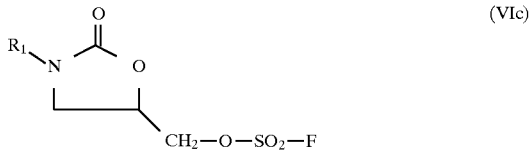
(VIc)

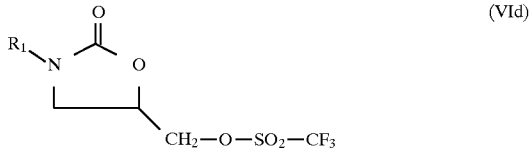
(VId)

and
  (2) contacting the oxazolidinone sulfonate (VI$_a$-VI$_d$) with ammonia at a pressure of less than about 30 psig.

DETAILED DESCRIPTION OF THE INVENTION

The process to produce the 5-hydroxymethyl substituted oxazolidinone alcohols (III) can use either the non-cyclic (S)-, (R)-dihydroxy compounds of formula (I) or any mixture thereof or (S)-, (R)-glycidol (IV) or any mixture to couple with the carbamate (IIA) or a trifluoroacetamide of formula (IIB).

The 5-hydroxymethyl substituted oxazolidinone alcohols (III) are useful intermediates to produce 5-aminomethyl substituted oxazolidinone amines (VII) which can be acylated to prepare pharmaceutically useful 5-acylamidomethyl substituted oxazolidinone (VIII) antibacterial agents. Because of an enantiomeric center, 5(R)-, 5(S)-acylamidomethyl substituted oxazolidinones (VIII) and mixtures thereof can be produced. The 5-acylamidomethyl substituted oxazolidinone (VIII) (S)-enantiomer has antibacterial activity, the (R)-enantiomer does not. The 5(S)-aminomethyl substituted oxazolidinone amine (VII) enantiomer is produced from the 5(R)-hydroxymethyl substituted oxazolidinone alcohol (III) enantiomer which is produced from the (S)-dihydroxy compound (I) or (S)-glycidol (IV). Therefore, the desired and preferred enantiomeric sequence is to use enantiomerically pure (S)-dihydroxy compound (I) or (S)-glycidol (IV) to give (R)-5-hydroxymethyl substituted oxazolidinone alcohol (III) which is used to give enantiomerically pure (S)-5-aminomethyl substituted oxazolidinone amine (VII) which is transformed to enantiomerically pure (S)-5-acylamidomethyl substituted oxazolidinone (VIII). However, it is readily apparent to one skilled in the art that one could easily perform the identical process steps with the opposite enantiomeric forms and at any point in the process invert an undesired enantiomeric configuration to the desired one. Therefore, using the chemistry of the claimed process with any of the enantiomeric forms is considered equivalent to the claimed processes.

The dihydroxy compounds, $M_1$—$CH_2$—$CH(OH)$—$CH_2$—$OH$, of formula (I) and glycidol compounds, $C^*H_2$—$C^*H$—$CH_2$—$OH$, of formula (IV) where the carbon atoms designated by an * are each bonded to the same oxygen atom (—O—) to form a three member ring, are known to those skilled in the art or can be readily prepared from known compounds by methods known to those skilled in the art. It is preferred that the hydroxy starting material be the dihydroxy compound (I). It is preferred that the dihydroxy compound (I) and the glycidol (IV) be the (S)-enantiomer. It is preferred that $M_1$ is Cl—; it is preferred that the dihydroxy compound (I) be claim 5, which can be purchased commercially.

The carbamates, $R_1$—NH—CO—O—$M_2$, of formula (IIA) and the trifluoroacetamide, $R_1$—NH—CO—$CF_3$, of formula (IIB) are either known to those skilled in the art or can readily be prepared from known compounds by methods known to those skilled in the art. The nature of the leaving group $M_2$ is not important since it is lost during the course of the reaction as is known to those skilled in the art. Operable $M_2$ (leaving groups) are those where —O—$M_2$ is a base whose acid has a $pk_a$ of between about 8 and about 24. Preferred $M_2$ includes $C_1$–$C_{20}$ alkyl,
$C_3$–$C_7$ cycloalkyl,
φ-optionally substituted with one or two $C_1$–$C_3$ alkyl or F—, Cl—, Br—, I—,
$CH_2$=CH—$CH_2$—,
$CH_3$—CH=CH—$CH_2$—,
$(CH_3)_2$C=CH—$CH_2$—,
$CH_2$=CH—,
φ-CH=CH—$CH_2$—,
φ-$CH_2$—optionally substituted on φ- with one or two —Cl, $C_1$–$C_4$ alkyl, —$NO_2$, —CN, —$CF_3$,
9-fluorenylmethyl,
$(Cl)_3$C—$CH_2$—,
2-trimethylsilylethyl,
φ-$CH_2$—$CH_2$—,
1-adamantyl,
$(φ)_2$CH—,
CH≡C—$C(CH_3)_2$—
2-furanylmethyl,
isobornyl, more preferred leaving groups are $C_1$–$C_4$ alkyl or benzyl. Any other leaving group which operates in a similar manner is considered equivalent to those identified above. The carbamate (IIA) and trifluoroacetamide (IIB) carry the aromatic/heteroaromatic group ($R_1$—) of the 5-hydroxymethyl substituted oxazolidinone alcohol (III). It is preferred that $R_1$ is phenyl substituted with one —F and one substituted amino group; it is more preferred that $R_1$ is 3-fluoro4-[4-(benzyloxycarbonyl)-1-piperazinyl]phenyl or 3-fluoro4-(4-morpholinyl)phenyl. Depending on the particular substituents in $R_1$, the groups may have to be protected as is known to those skilled in the art, by means known to those skilled in the art to prevent undesirable side reactions. For example, if the $R_1$ substituent has a free primary or secondary hydroxy group, it is not necessary, but preferable to protect it with an alcohol protecting group in the formation of the 5-hydroxymethyl substituted oxazolidinone alcohols (III). The unprotected alcohol will not in general interfere with the reaction of the dihydroxy compound (I) or glycidol (IV) with the carbamate (IIA) or trifluoroacetamide (IIB) to give the 5-hydroxymethyl substituted oxazolidinone alcohols (III). However, an unprotected alcohol will in general interfer with the conversion of the 5-hydroxymethyl substituted oxazolidinone alcohols (III) to the corresponding 5-aminomethyl substituted oxazolidinone amines (VII), because it is very difficult or impossible to selectively protect a primary or secondary alcohol on the $R_1$ functionality in the presence of another primary or secondary alcohol. Suitable alcohol protecting groups are well known to those skilled in the art, preferred are $C_1$–$C_5$ alkyl, φ-$CH_2$—, $CH_3$—O—$CH_2$—, $CH_3$—S—$CH_2$—, φ-$CH_2$—O—$CH_2$—, tetrahydropyranyl, $CH_3CH(-O-C_2H_5)-$, p-methoxybenzyl, p-methoxyphenyl, p-nitrobenzyl, $(φ)_3$C—, $(CH_3)_3$Si—, $[CH_3-CH(CH_3)]_3$Si—, φ$(CH_3)_2$Si—. These protecting groups are removed by means known to those skilled in the art. For example, if $R_1$ containes a hydroxy substituent, it must be protected during the transformation of the 5-hydroxymethyl substituted oxazolidinone alcohol (III) to the 5-aminomethyl substituted oxazolidinone amine (VII) or the 5-acylamidomethyl substituted oxazolidinone (VIII). If the $R_1$ substituent contains a free primary or secondary amino substituent it does not have to be protected during formation of the 5-hydroxymethyl substituted oxazolidinone alcohols (III) but must be protected during transformation of he 5-hydroxymethyl substituted oxazolidinone alcohols (III) to the corresponding 5-aminomethyl substituted oxazolidinone amines (VII) and the 5-acylamidomethyl substituted oxazolidinones (VIII). The reason is that the amino group will in general undergo an undesired side reaction during one or more of the steps involved in the transformation of the 5-hydroxymethyl substituted oxazolidinone alcohols (III) to the corresponding 5-acylamidomethyl substituted oxazolidinones (VIII). Therefore, it is preferable to protect any free amino substituent in the $R_1$ functionality prior to the reaction of the dihydroxy compound (I) or glycidol (IV) with the carbamate (IIA) or trifluoroacetamide (IIB). Amino protecting groups are very well known to those skilled in the art. Preferred amino protecting groups include:

(I) $C_1$–$C_4$ alkyl, (II) $\phi$-CH2—, (III) $(\phi)_3$C—, (IV) $R_a$—CO— where $R_a$ is (A) H—, (B) $C_1$–$C_4$ alkyl, (C) $C_5$–$C_7$ cycloalkyl, (D) ($C_1$–$C_5$ alkyl)—O—, (E) $Cl_3$C—$CH_2$—O—, (F) $H_2$C=CH—$CH_2$—O—, (G) $\phi$-CH=CH—$CH_2$—O—, (H) $\phi$-$CH_2$—O—, (I) p-methoxyphenyl-$CH_2$—O—, (J) p-nitrophenyl-$CH_2$—O—, (K) $\phi$-O—, (L) $CH_3$—CO—$CH_2$—, (M) $(CH_3)_3$Si—O—, (V) $R_b$—$SO_2$—where $R_b$ is: (A) ($C_1$ alkyl)-, (B) $\phi$-, (C) p-methylphenyl- and (D) $\phi$-$CH_2$—. A preferred amino protecting group is benzyloxycarbonyl which can be removed by catalytic hydrogenation as is known to those skilled in the art. There is nothing novel regarding the use of protecting groups in these reactions or the nature of the particular protecting groups. All this is well known to those skilled in the art. The protecting groups can be removed after the last reaction in which the protected substituent would be affected or carried along and removed after subsequent reactions as is known to those skilled in the art. For example, it my be preferable to carry the protecting group along until the final acylation step is completed, before removal, as is known to those skilled in the art. Optionally the $R_1$ substituent can be modified after the 5-acylamidomethyl substituted oxazolidinones (VIII) is produced depending on what chemical reactions are required as is known to those skilled in the art.

The reaction of either dihydroxy compounds (I) or glycidol (IV) with either the carbamates (IIA) or trifluoroacetamides (IIB) give the same 5-hydroxymethyl substituted oxazolidinone alcohols (III). The choice of whether to use a dihydroxy compound (I) or glycidol (IV) to produce a particular 5-hydroxymethyl substituted oxazolidinone alcohol (III) has to be made on a case by case basis. No starting material is preferred in all cases; there is no generally preferred way based on chemistry alone. The decision involves the commercial availability of the particular starting material, its chemical and enantiomeric purity, its cost, etc as is known to those skilled in the art.

One process of the present invention is the reaction of the dihydroxy compound (I) or glycidol (IV) with the carbamate (IIA) or trifluoroacetamides (IIB) in the presence of lithium cation ($Li^+$) and a base whose conjugate acid has a $pK_a$ of greater than about 8.

The processes requires about one molar equivalent of either the dihydroxy compound (I) or glycidol (IV)/ equivalent of carbamate (IIA) or trifluoroacetamides (IIB). The reaction requires a base, the nature of which is not critical so long as it is strong enough to deprotonate the carbamate (II). Operable bases are those whose conjugate acid has a $pK_a$ of greater than about 8. Preferred bases include compounds selected from the group consisting of:

alkoxy compounds of one thru seven carbon atoms, carbonate, methyl, sec-butyl and t-butyl carbanions, tri(alkyl)amines where the alkyl group is from 1 thru 4 carbon atoms, conjugate base of the carbamate (II),

DBU,

DBN,

N-methyl-piperidine,

N-methyl morpholine, 2,2,2-trichloroethoxide and $Cl_3$C—$CH_2$—$O^-$; most preferred bases are where the base is alkoxy of four or five carbon atoms. It is preferred that the four and five carbon alcohol bases be t-amylate or t-butoxide. Sodium or potassium bases in combination with a lithium salt (such as lithium chloride or lithium bromide) can be used forming the lithium cation and base in situ.

The nature of the solvent is not critical. Operable solvents include cyclic ethers such as THF, amides such as DMF and DMAC, amines such as triethylamine, acetonitrile, and alcohols such as t-amyl alcohol and t-butyl alcohol. The choice of solvent depends on the solubility of the carbamate (IIA) or trifluoroacetamide (IIB) as is known to those skilled in the art.

When the starting material is the dihydroxy compounds (I) it can be beneficial to react the dihydroxy compound (I) with an cyclizing agent prior to contacting with the carbamate (IIA) or trifluoroacetamide (IIB). The term "cyclizing agent" refers to a base that cyclizes the dihydroxy compound (I) to glycidol (IV). Operable cyclizing agents include bases whose acid has a $pk_a$ of greater than about 7; preferred cyclizing agents are sodium, potassium or lithium butoxide, sodium or potassium hydroxide, potassium carbonate, DBU, lithium, sodium and potassium amylate; most preferred is potassium t-butoxide. It is preferable to perform the reaction at <100°, more preferable to perform it at <70°, even more preferable to perform it at <50° and most preferable to perform it at <25°. The reaction can be performed at room temperature (about 20° to about 25°). At about 20°, the reaction requires about 8 hr to reach completion (in DMAC). If a faster reaction is desired, the reaction can be run at higher temperature. As stated above, differentiation between primary alcohols and secondary alcohols is difficult. In the cyclization reaction, a simple alcohol is formed. For instance, benzyl alcohol is formed when a benzyl carbonate is subjected to the cyclization conditions. Removal of this alcohol is necessary to the success of the alcohol to amine conversion. This is accomplished by crystallization using ethyl acetate/heptane (½). The benzyl alcohol stays in solution and the desired oxazolidinone alcohol is isolated as a solid.

CHART C discloses the processes of transforming the 5-hydroxymethyl substituted oxazolidinone alcohols (III) to the corresponding 5-aminomethyl substituted oxazolidinone amines (VII). The situation of protecting the alcohol and/or amino groups on the $R_1$ functionality was discussed above. The 5-hydroxymethyl substituted oxazolidinone alcohols (III) are contacted with a sulfonylating agent ($V_a$–$V_d$) of four types. These are $M_3$—$SO_2$—$C_6H_{n3}(NO_2)_{n1}Cl_{n2}$ ($V_a$), $O[—SO_2—C_6H_{n3}(NO_2)_{n1}Cl_{n2}]_2$ ($V_b$), $O(SO_2—F)_2$ ($V_c$) and $O(SO_2—CF_3)_2$($V_d$). $M_3$ is a leaving group which includes Cl— or Br—; it is preferred that $M_3$ be Cl—. The 5-hydroxymethyl substituted oxazolidinones (III) are contacted with a sulfonylating agent ($V_a$–$V_d$) to form a oxazolidinone sulfonate ($VI_a$–$VI_d$) intermediate.

The sulfonation reaction of converting the 5-hydroxymethyl substituted oxazolidinones (III) to the corresponding oxazolidinone sulfonates (VI) is performed by contacting the 5-hydroxymethyl substituted oxazolidinones (III) with at least one molar equivalent of the sulfonylating agent $V_a$–$V_d$) in the presence of a base in an inert solvent at about 0°. Operable bases include triethylamine, tributylamine, diisopropylethylamine, DABCO, DBU, DBN, n-butyl lithium, ethyl magnesium chloride and the equivalents thereof; preferred is triethylamine. Inert solvents include most organic solvents such as methylene chloride, THF, DMA, DMF, ethyl acetate, and the equivalent thereof; preferred is methylene chloride.

The ammonolysis reaction of the conversion of the oxazolidinone sulfonates (VI) to the corresponding 5-aminomethyl substituted oxazolidinone amines (VII) is performed under open or non-sealed conditions or under sealed conditions although it is preferred to be performed under sealed conditions.

In either case the ammonolysis reaction is carried out by contacting the oxazolidinone sulfonates (VI) with ammonia (preferably aqueous) preferably with a solvent or mixture of solvents. Preferred solvents are those that dissolve both the oxazolidinone sulfonates (VI) and the aqueous ammonia because by dissolving both contact between them is insured. However, the process is also operable with solvents that only partially dissolve the oxazolidinone sulfonates (VI), the disadvantage is that the reaction in general is slower. In the case of the the m-nitrobenenesulfonates, the preferred solvent is a mixture of acetonitrile/isopropanol or THF/isopropanol. The system is put under reduced pressure. The system is then closed or sealed, and the ammonia (preferably aqueous ammonia) is added and heated to less than 50°, preferably to less than 40°, preferably to about 38° (about 3 psig). At about 38°–40° the pressure is about 0 to about 10 psig, which is well below the ceiling pressure rating of general purpose reactors. Under these conditions, at about 60°, the psig is about 20. It is preferred that the ammonolysis reaction be performed at a pressure of about 0 to about 20 psig, preferably at about 0 to about 5 psig and at about 60° or less. Alternatively, the reaction is performed in an open system at reflux. In this case the temperature will be slightly lower and the reaction will require slightly longer to reach completion. The ammonia can be either aqueous, alcoholic or anhydrous; however, aqueous ammonia is preferred.

Alternatively, the contacting with aqueous ammonia can be performed in the presence of an aromatic aldehyde (IX, Ar—CHO), preferably salicylaldehyde. The 5-aminomethyl substituted oxazolidinone amines (VII) and the aldehyde (IX) form a Schiff base of the formula (oxazolidinone-N=CH—Ar) which is then hydrolyzed with aqueous acid, as is known to those skilled in the art, to give the desired 5-aminomethyl substituted oxazolidinone amines (VII). The aromatic aldehyde (IX) is useful in suppressing dimer formation.

The 5-aminomethyl substituted oxazolidinone amines (VII) are acylated by known means such as acyl halides or acyl anhydrides to form the corresponding 5-acylamidomethyl substituted oxazolidinone (VIII), see CHART D. Any alcohol or amino protecting groups must be removed after the 5-acylamidomethyl substituted oxazolidinones (VIII) are produced. However, they can be removed earlier in the reaction sequence depending on the particular substituents in question as is known to those skilled in the art.

The 5-acylamidomethyl substituted oxazolidinones (VIII) are known to be antibacterial pharmaceutical agents. $R_2$ is selected from the group consisting of —H, $C_1$–$C_{12}$ alkyl optionally substituted with one or more halogens, ($C_3$–$C_7$) cyclo($C_5$–$C_9$)alkyl or —O—$R_{2a}$ where $R_{2a}$ is $C_1$–$C_6$ alkyl. It is preferred that $R_2$ is $C_1$ alkyl.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$) H. Groups $R_i$ and $R_j$ would represent monovalent variable substituents if attached to the formula $CH_3$—$CH_2$—C($R_i$) ($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_j$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)- 1-piperazinyl can be represented by —N*—($CH_2$)$_2$—N($C_2H_5$)—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —C($\alpha$-$R_{i-j}$)($\beta$-$R_{i-k}$)-. For example, when the bivalent variable $R_6$, —C(=$R_6$)— is defined to consist of two monovalent variable substituents, the two monovalent variable substituents are $\alpha$-$R_{6-1}$:$\beta$-$R_{6-2}$, ... $\alpha$-$R_{6-9}$:$\beta$-$R_{6-10}$, etc, giving —C($\alpha$-$R_{6-1}$)($\beta$-$R_{6-2}$)—, .... —C($\alpha$-$R_{6-9}$)($\beta$-$R_{6-10}$)—, etc. Likewise, for the bivalent variable $R_{11}$, —C(=$R_{11}$)—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1(R_i)$H—$C_2(R_j)$H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO—. . ." means a lactone in which the carbonyl is bonded to $C_2$. However, when designated ". . . $R_j$ and $R_i$ are taken together to form —CO—O—$CH_2$—$CH_2$—the convention means a lactone in which the carbonyl is bonded to $C_i$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxy-carbonyl because the "$C_1$–$C_3$" refers only to the carbon atom content of the alkoxy group. Similarly while both $C_2$–$C_6$ alkoxyalkyl and ($C_1$–$C_3$) alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

THF refers to tetrahydrofuran.

DMF refers to dimethylformamide.

DBU refers to 1,8-diazabicyclo[5.4.0]undec-7-ene.

DBN refers to 1,5-diazabicyclo[4.3.0]non-5-ene.

DABCO refers to 1,4-diazabicyclo[2.2.2]octane.

DMA refers to dimethylacetamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

IR refers to infrared spectroscopy.

CMR refers to $^{13}$C magnetic resonance spectroscopy, chemical shifts are reported in ppm ($\delta$) downfield from TMS.

NMR refers to nuclear (proton) magnetic resonance spectroscopy, chemical shifts are reported in ppm ($\delta$) downfield from tetramethylsilane.

-$\phi$refers to phenyl ($C_6H_5$).

$[\alpha]_D^{25}$ refers to the angle of rotation of plane polarized light (specific optical rotation) at 25° with the sodium D line (589A).

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

NNNNNN—NN—N refers to Chemical Abstracts Service (CAS, Columbus, Ohio) registry numbers where each "N" is an integer from 0 thru 9, but deleting leading zeros in the 6-digit portion of the number. Registry numbers are assigned to a particular chemical compound by CAS criteria, provided that the compound has been found to exist and it has been characterized in some way. Compounds published from approximately 1967 to the present are registered publicly and the registry number is the key to finding references in the CAS data base for such a registered compound. The CAS data base is publicly available from several database vendors such as STN International, System Development Corporation (SDC) Orbit Search Service, Lockheed Dialog, Bibliographic Retrieval Systems, Questrel, etc. CAS registry numbers are included in the EXAMPLES for some of the compounds which have been registered. "psig" refers to "gauge pressure" equal to pressure (in psi) minus 1 atmosphere (14.7 psi).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

(R)-[N-3-[3-Fluoro-4-[N-1-(4-carbobenzoxy) piperazinyl]phenyl]-2-oxo-5-oxazolidinyl]methanol (III)

A mixture of N-carbobenzoxy-3-fluoro-4-(N-carbobenzoxypiperazinyl)aniline (II, J. Med. Chem., 39(3), 673 (1996)), 100 g of 98.4% pure material, 0.2133 moles) in DMAC (300 ml) is cooled to 0°. In a separate flask, a mixture of t-amyl alcohol (75 ml, 60.37 g, 0.685 moles, 3.23 eq) and heptane (75 ml) is cooled to −10° and treated with n-butyllithium in heptane (290 ml, 203 g of 14.4% wt/v solution, containing 29.2 g or 0.456 moles=2/15 eq of n-butyllithium), keeping the temperature below 10°. The lithium t-amylate mixture is then added to the N-carbobenzoxy-3-fluoro4-(N-carbobenzoxypiperazinyl) aniline (II) keeping the temperature below 10°.

Neat S-(+)-3-chloro-1,2-propanediol (I, CAS #60827-45-4, 22 ml, 29.1 g, 0.263 moles, 1.24 eq) is then added, rinsing with a small amount of heptane. The reaction mixture is then stirred at 20°–25° and monitored by TLC (methanol/methylene chloride; 5/95) until the reaction is complete. The reaction mixture is then added to a mixture of acetic acid (40 ml, 42.0 g, 0.699 moles, 3.29 eq) in methanol (700 ml) and water (700 ml). The slurry formed is stirred at 20°–25° for 30 min, cooled to 0°, stirred at 0° for 30 min, and filtered. The cake is washed with methanol/water (50/50) and dried under reduced pressure to give the title compound, TLC (methylene chloride/methanol, 95/5) $R_f$=0.43.

Example 2

(R)-[N-3-[3-Fluoro-4-[N-1-(4-carbobenzoxy) piperazinyl]phenyl]-2-oxo-5-oxazolidinyl]methanol (III)

t-Amyl alcohol (0.967 g, 10.97 mmol, 2.571 eq) is cooled to −10°. Butyl lithium (4.3 ml, 2.5M in hexanes, 10.8 mmol, 2.5 eq) is added with agitation while maintaining the temperature at less than 5°.

N-Carbobenzoxy-3-fluoro-4-(N-carbobenzoxypiperazinyl)aniline (II, 1.9780 g, 4.267 mmol, 1.000 eq) and dimethylacetamide (6.2 ml) are mixed, agitated and cooled to −25° to give a thin slurry. The lithium t-amylate mixture is then added to the N-benzyloxycarbonyl-3-fluoro-4-((4-benzyloxycarbonyl)-1-piperazinyl)aniline (II) mixture while maintaining less than −20°. The resultant mixture is warmed to 0° and S-(+)-3-chloro-1,2-propanediol (I, 0.5672 g, 5.131 mmol, 1.20 eq) is added. The resultant mixture is warmed to 21° and stirred for 7.5 hrs. The reaction mixture is added to a methanol (28 ml) and glacial acetic acid (0.73 ml, 12.75 mmol) mixture at 20°–22°. The resulting slurry is then cooled to −30° and the product collected by vacuum filtration and washed with −30° methanol. The solids are dried in a stream of nitrogen to give the title compound, TLC (eluant chloroform/methanol, 90/10), $R_f$=0.67; CMR (CDCl$_3$) 43.91, 46.39, 50.58, 62.60, 67.29, 72.89, 107.21, 107.56, 113.85, 119.36, 127.92, 128.09, 128.52, 133.51, 133.65, 136.05, 136.17, 136.57, 153.91, 154.80, 155.25 and 157.17 δ; NMR (CDCl$_3$) 7.43, 7.31–7.37, 7.09, 6.88, 5.15, 4.67–4.90, 3.89–3.99, 3.67–3.74, 3.66, 3.25 and 2.98 δ; MS (CI, m/e)=430 (100%, P+1).

Example 3

(R)-[N-3-(3-Fluoro-4-(4-morpholinylphenyl)-2-oxo-5-oxazolidinyl]methanol (III)

Tetrahydrofuran (3.0 ml) and t-amyl alcohol (0.66 ml, 6.03 mmol, 2.00 eq) are mixed. Butyl lithium (1.8 ml, 2.5M in hexanes, 4.55 mmol, 1.5 eq) is added with agitation and while maintaining less than 2.5°.

N-Carbobenzoxy-3-fluoro-4-morpholinylaniline (II, J. Med. Chem., 39(3), 673 (1996), 0.9942 g, 3.00 mmol, 1.000 eq) and tetrahydrofuran (3.5 ml) are mixture agitated and cooled. The lithium t-amylate mixture is then added to the carbamate (II) mixture while maintaining the temperature less than 8° and rinsed in with tetrahydrofuran (1 ml).

Tetrahydrofuran (3.2 ml) and S-(+)-3-chloro-1,2-propanediol (I, 0.299 ml, 3.58 mmol, 1.19 eq) are mixed. The mixture is cooled to −16° and potassium t-butoxide (3.2 ml, 1.0M in tetrahydrofuran, 3.2 mmol, 1.07 eq) is added while maintaining the temperature at less than −10°. The resulting slurry is stirred at −14° to 0° for 1 hr then added to the lithium anion mixture while maintaining both mixtures at 0°, then rinsed in with THF (2 ml). The resultant slurry is stirred at 20°–23° for 2 hr then cooled to 6° and a mixture of citric acid monohydrate (0.4459 g, 2.122 mmol, 0.705 eq) in water (10 ml) is added. The resultant liquid phases are separated and the lower aqueous phase is washed with ethyl acetate (12 ml). The organic layers are combined and solvent is removed under reduced pressure until a net weight of 9.73 g remains. Heptane (10 ml) and water (5 ml) are added and solvent is removed by reduced pressure until a total volume of 5 ml remains. The precipitated product is collected by vacuum filtration and washed with water (7 ml). The solids are dried in a stream of nitrogen to give the title compound, TLC (chloroform/methanol, 95/5) $R_f$=0.23; CMR (CDCl$_3$) 46.42, 51.01, 62.58, 73.07, 107.29, 107.64, 113.94, 118.80, 118.85, 128.28, 128.61, 133.15, 133.29, 136.26, 136.38, 153.82, 154.92 and 157.08 δ; NMR (CDCl$_3$) 7.42, 7.32–7.37, 7.10, 4.67–4.75, 3.90–4.00, 3.86, 3.70–3.73, 3.44 and 3.03 δ; MS (El, m/e)=296.

Alternatively, the crude product can be extracted with methylene chloride. The solvent is removed under reduced pressure. The solids are redissolved in hot ethyl acetate, heptane is added, the mixture is cooled and the title compound is recovered.

Example 4

(R)-[N-3-[3-Fluoro-4-[N-1-(4-carbobenzoxy) piperazinyl]phenyl]-2-oxo-5-oxazolidinyl]methanol (III)

A solution of t-amyl alcohol (75 ml, 60.3 g, 0.68 m) and heptane (75 ml) is stirred and cooled to −10°. The mixture is treated with n-butyl lithium in heptane (1.6 M, 0.46 m, 290 ml) over a 30 min period while maintaining a temp <10°. After 30 min, the mixture of lithium t-amylate is added to a mixture of N-carbobenzoxy-3-fluoro-4-(N-carbobenzoxypiperazinyl)aniline (II, 100 g, 0.22 m) and dimethylacetamide (300 ml) at 0° while maintaining a temp <10°. The mixture is stirred 30 min, then treated with S-(+)-3-chloro-1,2-propanediol (I, 22 ml, 0.26 m). The cooling is removed, and the mixture is allowed to warm to 20°–25°. The reaction is monitored by TLC and is judged complete after about 8 hr. The reaction mixture is poured into a mixture of methanol (700 ml), water (700 ml) and acetic acid (40 ml) and stirred for 30 min at 20°–25°, then stirred for 30 min with cooling to 0°. The mixture is filtered, washed with aqueous methanol (50/50) and dried under reduced pressure at 45° to give the title compound, TLC (silica gel; methanol/methylene chloride, 5/95) $R_f$=0.5. (90.3% yield).

Example 5

3-Nitrobenzenesulfonate ester (R)-[N-3-[3-fluoro-4-(N-1-(4-carbobenzoxy) piperazinyl]-phenyl]-2-oxo-5-oxazolidinyl]methanol (VI)

A mixture of (R)-[N-3-[3-fluoro-4-[N-1-(4-carbobenzoxy)piperazinyl]phenyl]-2-oxo-5-oxazolidinyl]methanol (III, EXAMPLE 1, 43 g, 0.1 m) and methylene chloride (500 ml) is treated with triethylamine (32 ml, 0.23 m) and cooled to −5°. To this mixture is added a mixture of 3-nitrobenzenesulfonyl chloride (CAS #121-51-7, 32 g, 0.14 ml) in methylene chloride (60 ml) while maintaining the temp <10° over a 1 hr period. The reaction is monitored by TLC and judged complete after 45 min. The mixture is diluted with methylene chloride (500 ml) and then washed with water (2×600 ml). The organic phase is then washed with hydrochloric acid (1N, 400 ml) and concentrated to a thick residue. The residue is diluted with methanol (200 ml) and stirred for 1.5 hr. The solids are filtered, washed with methanol and dried under reduced pressure at 40° overnight to give the title compound, TLC (silica gel; methanol/methylene chloride, 5/95) $R_f$=0.75.

Example 6

(S)-N-[[3-[3-Fluoro-4-[N-1-(4-carbobenzoxy) piperazinyl]-phenyl]-2-oxo-5-oxazolidinyl]methyl] acetamide (VII)

A slurry of 3-nitrobenzenesulfonate ester (R)-[N-3-[3-fluoro-4-(N-1-(4-carbobenzoxy) piperazinyl]-phenyl]-2-oxo-5-oxazolidinyl]methanol (VI, EXAMPLE 5, 50 g, 0.081 ml), isopropanol (250 ml), acetonitrile (400 ml) and aqueous ammonium hydroxide (29% ammonia by wt, 500 ml) is heated at 40° for 3.5 hr. The mixture is then treated with more aqueous ammonia (100 ml) and stirred for 20 hr. The reaction is monitored by TLC and judged complete at this time. The mixture is concentrated under reduced pressure with heat and suspended in methylene chloride/water (1250 ml/750 ml). The phases are separated and the organic phase concentrated to give a residue.

The residue is dissolved in methylene chloride (2 l) and treated with triethylamine (20 ml, 0.14 m). The mixture is then treated with acetic anhydride (10 ml, 0.11 m) at 20°–25° over 10 min. The acetylation is monitored by TLC and judged complete after 15 min. The organic mixture is washed with water (2×400 ml) then concentrated to a solid. The solids are recrystallized from ethanol (400 ml), filtered and dried under reduced pressure to give the title compound, TLC (silica gel; methanol/methylene chloride, 5/95) $R_f$=0.6.

Example 7

(S)-N-[[3-[3-fluoro-4 1-piperazinyl)phenyl]-2-oxo-5-oxazolidinyl]methyl]acetamide hydrochloride (intermediate)

A mixture of (S)-N-[[3-[3-fluoro-4-[N-1-4-carbobenzoxy)piperazinyl]-phenyl]-2-oxo-5-oxazolidinyl] methyl]acetamide (VII, EXAMPLE 6, 35 kg, 74.5 moles), palladium on carbon (5%, 10 kg, 50% water wet), methanol (550 l) and tetrahydrofuran (250 l) is agitated at 22° to 42° under a 42°–50° psi hydrogen atmosphere. After 31 hours TLC analysis indicated complete reaction and the hydrogen atmosphere was replaced with nitrogen. The catalyst is removed by filtration and the filtrate concentrated under vacuum to 100 l. To the resulting mixture, cooled to 2°, is added methanol (50 l) then a mixture of methanol (100 l) and acetyl chloride (6.04 kg, 77 moles) at −2° to 6°. The resulting mixture is stirred 90 minutes then concentrated under vacuum to 60 l, diluted with acetone (100 l) and concentrated further to 100 l. The resulting slurry is diluted with acetone (200 l) and stirred 15 hr at 16°. The solids are collected on a filter, washed with acetone (50 l) and dried under reduced pressure at 20°–25° to give the desired product. It is dissolved in methanol (56 l) at 53°, diluted with acetone (150 l), stirred 30 minutes at 48° then cooled to 15° and stirred 18 hr. The solids are collected on a filter, washed with acetone (50 l) and dried under reduced pressure at 20°–25° to give the title compound, NMR (CDCl$_3$) 7.56–7.45, 7.31, 7.12–6.86, 4.79, 4.09–4.0, 3.81, 3.62, 3.40–3.11 and 2.01 δ.

Example 8

(S)-N-[[3-[3-fluoro-4-[4-(hydroxyacetyl)-1-piperazinyl]-phenyl]-2-oxo-5-oxazolidinyl]methyl]-acetamide sesquihydrate (VIII)

To a stirred mixture of (S)-N-[[3-[3-fluoro-4(-1-piperazinyl)phenyl]-2-oxo-5-oxazolidinyl]methyl] acetamide hydrochloride (EXAMPLE 7, 16.2 kg, 43.5 moles), tetrahydrofuran (205 kg) and triethylamine (10.1 kg, 100 moles) is added acetoxyacetyl chloride (6.5 kg, 47.8 moles) in tetrahydrofuran (11.1 kg) over 35 minutes keeping the temperature at 22°–23°. After 40 minutes, at which time TLC and HPLC analysis indicated complete formation of the acetoxyacetamide intermediate, the mixture is concentrated under reduced pressure to 30 l, diluted with methanol (100 l) and concentrated to 30 l. To the residue is added methanol (25 l) and an aqueous solution of potassium carbonate (5.6 kg in 56 l). The resulting mixture is stirred 20 hr at 22°–25° at which time TLC and HPLC analysis indicates the reaction is complete. The pH is adjusted to 7–7.5 with hydrochloric acid (4N, 14.3 l). The mixture is stirred 18 hr at 15°–22° then 3 hrs at 2°–5°. The solids are collected on a filter, washed with water (68 l) and dried at 20°–25° with recycled nitrogen to give the desired product. The crude product is dissolved in water (225 l) at 60°–70°, clarified through a 0.6 micron filter, diluted with water rinse (55 l) and stirred 17 hrs. at 15°. The solids are collected on a filter, washed with water at 15° and dried at 45° with recycled nitrogen to a water content of 0.33%. These solids are dissolved in a solution of ethyl acetate (143 l), methanol (65 l) and water (1.95 l) at 60°–65°. The solution is cooled to 15°–25° and stirred 16 hrs for crystallization. The solids are collected on a filter, washed with ethyl acetate (75 l) and dried with 45° nitrogen to give the desired product. The product is recrystallized two more times from water (147 l then 133 l) at 60°–70°, clarified each time through a 0.6 micron filter and rinsed with water (40 l and 30 l). The solids are dried on the filter at 30° with recycled nitrogen to give, after deagglomeration through a mill, the title compound as the sesquihydrate (6.45% water), TLC (silica gel; methanol/methylene chloride, 5/95) $R_f$=0.45; $[\alpha]_D$=−20° (c=1.0, ethanol).

Example 9

3-Nitrobenzenesulfonate ester (R)-[N-3-[3-fluoro-4-(N-1-(4-carbobenzoxy)piperazinyl]-phenyl]-2-oxo-5-oxazolidinyl]methanol (VI)

To a slurry of (R)-[N-3-[3-fluoro-4-[N-1-(4-carbobenzoxy)piperazinyl]phenyl]-2-oxo-5-oxazolidinyl]methanol (III, EXAMPLE 1, 5.086 g, 11.86 mmol) in methylene chloride (50 mL) and triethylamine (2.0 mL, 14.38 mmol) at 0° is added dropwise over 6 minutes a solution of 3-nitrobenzene sulfonyl chloride (V) in methylene chloride (0.356M, 33.4 mL, 11.89 mmol). After stirring for 3.25 hrs, an additional 3.4 mL (1.21 mmol) of the 0.356M solution of 3-nitrobenzene sulfonyl chloride (V) is added. After stirring for 1.75 hrs, hydrochloric acid (1N, 50 mL) is added. The phases are separated and the aqueous phase is extracted with methylene chloride. The combined organic phases are washed with saline, dried over magnesium sulfate and concentrated. The concentrate is crystallized from hot methylene chloride/methanol to give the title compound, mp=155°–157°; NMR (CDCl$_3$, 400 MHz) 8.72, 8.51, 8.23, 7.81, 7.35, 7.01, 6.91, 5.17, 4.85, 4.44, 4.39, 4.09, 3.85, 3.68 and 3.01 δ; CMR (CDCl$_3$, 100 MHz) 44.26, 46.81, 50.91, 67.64, 69.54, 69.91, 107.85, 114.32, 119.85, 123.55, 128.30, 128.47, 128.91, 129.15, 131.51, 133.71, 136.99, 137.70, 148.71, 153.62, 155.57 and 155.88 δ; IR (mineral oil mull) 1744, 1703, 1528, 1520, 1367, 1347 and 1192 cm$^{-1}$; MS (EI, M/Z) 614, 411, 107, 91, 79, 65 and 56; $[\alpha]_D$=−78° (c=0.9812, CHCl$_3$); TLC (ethyl acetate/hexane, 3/1) $R_f$=0.43.

Example 10

2-nitrobenzenesulfonate ester (R)-[N-3-[3-Fluoro-4-[N-1(4-carbobenzoxy) piperazinyl]phenyl]-2-oxo-5-oxazolidinyl]methanol (VI)

Following the general procedure of EXAMPLE 5 (for the 3-nitrobenzenesulfonyl ester, (VI)) and making non-critical variations, (R)-[N-3-[3-fluoro-4-[N-1-(4-carbobenzoxy) piperazinyl]phenyl]-2-oxo-5-oxazolidinyl]methanol (III, EXAMPLE 1, 1.106 g, 2.578 mmol) is treated with triethyl amine (0.54 mL, 3.882 mmol) and commercial grade 2-nitrobenzenesulfonyl chloride (V, 679 mg, 3.064 mmol) to give the title compound, NMR (CDCl$_3$, 400 MHz) 8.15, 7.82, 7.37, 7.06, 6.94, 5.17, 4,89, 4.59, 4.50, 4.10, 3.98, 3.69 and 3.03 δ; IR (mineral oil mull) 1757, 1697, 1517, 1445, 1423, 1376, 1237 and 1188 cm$^{-1}$; MS (EI, M/Z; rel. abundance): 614 (18.3, M$^+$), 91 (100), 69 (23.8) and 56 (52.9); TLC (ethyl acetate/hexane, 3/1) $R_f$=0.31.

Example 11

2,4-dinitrobenzenesulfonate ester (R)-[N-3-[3-Fluoro-4-[N-1-(4-carbobenzoxy) piperazinyl] phenyl]-2-oxo-5-oxazolidinyl]methanol (VI)

Following the general procedure of EXAMPLE 5 (for the 3-nitrobenzenesulfonyl ester) and making non-critical variations (R)-[N-3-[3-Fluoro-4-[N-1-(4-carbobenzoxy) piperazinyl]phenyl]-2-oxo-5-oxazolidinyl]methanol (III, EXAMPLE 1, 1.094 g, 2.550 mmol) is treated with triethyl amine (0.55 ML, 3.950 mmol) and commercial grade 2,4-dinitrobenzenesulfonyl chloride (833 mg, 3.124 mmol) to give the title compound, NMR (CDCl$_3$, 400 MHz) 8.59, 8.38, 7.35, 7.02, 5.17, 4.88, 4.74, 4.58, 4.10, 3.98, 3.71, and 3.05 δ; IR (mineral oil mull) 1756, 1697, 1554, 1541, 1517, 1351, 1237 and 1189 cm$^{-1}$; MS (FAB, M/Z, rel. abundance) 660 (21.3, [M+H]$^+$), 659 (24.2, M$^+$), 102 (76.5) and 91 (100); TLC (ethyl acetate/hexane, 3/1) $R_f$=0.41.

Example 12

(R)-[N-3-[3-Fluoro-4-[N-1-(4-carbobenzoxy) piperazinyl]phenyl]-2-oxo-5-oxazolidinyl]methanol 4-chlorobenzenesulfonate ester (VI)

To a slurry of (R)-[N-3-[3-fluoro-4-[N-1-(4-carbobenzoxy)piperazinyl]phenyl]-2-oxo-5-oxazolidinyl] methanol (III, EXAMPLE 1, 3.450 g, 8.034 mmol) in methylene chloride (40 ml) and triethylamine (2.55 ml, 18.3 mmol) at −12° is added 4-chlorobenzenesulfonyl chloride (V, Aldrich Chemical Co.—commercial, 2.298 g, 10.88 mmol) as a solid all at once. The mixture is stirred in a 0° bath for 2.5 hrs then washed with water (2×35 ml), and 1N hydrochloric acid (35 ml). The organic extracts are concentrated to 20 ml total volume and methanol (50 ml) is added. The precipitate is collected by vacuum filtration, washed with methanol, dried and redissolved in methylene chloride (55 ml). The mixture is concentrated to a slurry of 32 g weight and methanol (11 ml) is added. The precipitate is collected by vacuum filtration, washed with methanol and dried. The solids are then dissolved in methylene chloride (58 ml) and column chromatographed (silica column, 93 g 40–63μ; eluted with 450 ml each of following ethyl acetate/cyclohexane mixtures 25/75; 35/65; 45/55; 55/45; collect last 50% of eluent). The collected eluent is concentrated to 200 ml and 200 ml heptane is added. The precipitate is collected by vacuum filtration and dried to give the title compound; TLC (silica gel; methanol/ chloroform 5/95) $R_f$=0.53; MS (FAB, M/Z)=604.7 (100%, [P+H]$^+$); NMR (DMSO-d$_6$, 300 MHz) 7.93, 6.7, 7.75, 7.48–7.32, 7.12–7.03, 5.12, 4.93–4.92, 4.40, 4.09, 3.69, 3.57 and 2.96 δ; CMR (DMSO-d$_6$, 75 MHz) 43.51, 45.84, 50.22, 66.33, 69.75, 70.75, 106.63, 114.08, 119.83, 127.59, 127.87, 128.43, 129.62, 130.00, 133.31, 133.63, 135.52, 136.84, 139.63, 153.54, 154.40 and 154.62 8.

Example 13

(R)-[N-3-[3-Fluoro-4-[N-1-(4-carbobenzoxy) piperazinyl]phenyl]-2-oxo-5-oxazolidinyl]methanol 2,5-dichlorobenzenesulfonate ester (VI)

To a slurry of (R)-[N-3-[3-fluoro-4-[N-1-(4-carbobenzoxy)piperazinyl]phenyl]-2-oxo-5-oxazolidinyl] methanol (III, EXAMPLE 1, 3.439 g, 8.008 mmol) in methylene chloride (40 ml) and triethylamine (2.55 ml, 18.3 mmol) at −8° is added 2,5-dichlorobenzenesulfonyl chloride (V, Aldrich Chemical Co.—commercial, 2.675 g, 10.90 mmol) as a solid all at once. The mixture is stirred in a 0° bath for 2.5 hrs then washed with water (2×35 ml), and 1N hydrochloric acid (35 ml). The organic extracts are then concentrated to 12.0 g which is column chromatographed (silican column, 108 g, 40–63μ; eluted with 450 ml each of following ethyl acetate/cyclohexane mixtures 10/90, 20/80, 30/70, 40/60 and 60/40 collecting the last 20% of eluent). The collected eluent is concentrated and 300 ml methanol is added. The precipitate is collected by vacuum filtration, washed with methanol and dried to give the title compound, TLC (silica gel; methanol/chloroform 5/95) $R_f$=0.66; MS (FAB, M/Z)=638.6 (100%, [P+H]$^+$); NMR (CDCl$_3$, 300 MHz) 8.04, 7.57–7.32, 7.06, 6.91, 5.16, 4.89–4.47, 4.42, 4.08, 3.93, 3.67 and 3.01 δ; CMR (CDCl$_3$, 75 MHz) 43.93, 45.51, 50.56, 67.26, 69.16, 69.46, 107.55, 113.98, 119.41, 127.92, 128.10, 128.54, 131.21, 131.46, 132.97, 133.44, 133 50, 134.68, 135.15, 136.45, 136.61, 153.36, 155.22 and 155.53 δ.

Example 14

(R)-[N-3-[3-Fluoro-4-[N-1-(4-carbobenzoxy) piperazinyl]phenyl]-2-oxo-5-oxazolidinyl]methanol 4-nitrobenzenesulfonate ester (VI)

To a slurry of (R)-[N-3-[3-fluoro-4-[N-1-(4-carbobenzoxy)piperazinyl]phenyl]-2-oxo-5-oxazolidinyl] methanol (III, EXAMPLE 1, 3.437 g, 8.003 mmol) and 4-nitrobenzenesulfonyl chloride (V, 75% pure technical material, Aldrich Chemical Co.—commercial, 3.077 g, 10.41 mmol) in methylene chloride (32 ml) at 0° is added triethylamine (2.23 ml, 16.0 mmol). The mixture is stirred in a 0° bath for 1 hr then water (1 ml) is added and the mixture stirred at 20°–25° for 30 min. Methylene chloride (75 ml) is added and the mixture washed with hydrochloric acid (5%, 50 ml), then sodium bicarbonate (5%, 50 ml) and dried on magnesium sulfate. The organic extracts are then concentrated and the concentrate is taken up in boiling ethyl acetate/cyclohexane (1/1, 10 ml) and column chromatographed (silica gel, 4 cm×6", 40–63μ; eluting with about 400 ml each of following ethyl acetate/cyclohexane mixtures 20/80, 30/70, 40/60, 50/50, 60/40 and 70:30 collecting the last approximate 45% of eluent). The appropriate fractions are combined and concentrated to a solid which is dissolved in 70 ml methylene chloride and 50 ml ethyl acetate. The mixture is concentrated to 50 ml twice and cyclohexane (50 ml) is added after each concentration. The precipitate is collected by vacuum filtration, washed with cyclohexane and dried to give the title compound, TLC (silica gel; ethyl acetate/cyclohexane 60/40) $R_f$=0.37; NMR (CDCl$_3$, 300 MHz) 8.36, 8.07, 7.38–7.29, 7.03, 6.89, 5.15, 4.86–4.80, 4.39, 4.07, 3.80, 3.67 and 3.00 δ; CMR (CDCl$_3$, 75 MHz) 43.85, 46.34, 50.45, 67.20, 69.17, 69.57, 107.64, 113.88, 119.34, 124.63, 127.85, 128.05, 128.49, 129.26, 132.67, 136.48, 136.57, 140.75, 150.95, 153.29, 155.14 and 155.40 δ.

Example 15

(S)-[N-3-[3-Fluoro-4-[N-1-(4-carbobenzoxy) piperazinyl]phenyl]-2-oxo-5-oxazolidinyl] methylamine (VII)

Under nitrogen at 40° 3-nitrobenzenesulfonate ester (R)-[N-3-[3-fluoro-4-(N-1-(4-carbobenzoxy)piperazinyl]-phenyl]-2-oxo-5-oxazolidinyl]methanol (VI, EXAMPLE 5, 1.0099 g, 1.643 mmol), isopropanol (5.6 ml), acetonitrile (9.0 ml), benzaldehyde (0.50 ml, 4.92 mmol) and aqueous ammonia (29.8 wt % 9.5 ml, 148.6 mmol) are mixed. The mixture is stirred at 40° for 21.5 hrs, then concentrated under reduced pressure. Toluene (13.3 ml) and ethanol (6.0 ml) are added and the mixture warmed in a 70° bath. Citric acid monohydrate (2.433 g, 11.58 mmol) was then added over 3.5 hrs and the phases separated at 64°. The organic phase is washed with water (2.5 ml) at 64°. The combined aqueous layers are washed with toluene (10 ml) at 64°.Toluene (10 ml) is then added to the aqueous and the mixture cooled to 0°. The precipitate is collected by vacuum filtration, washed with 0° toluene (10 ml) and 0° water (10 ml) and dried to a solid. A portion of this solid (0.7301 g) is slurried in water (10 ml) and methylene chloride (10 ml) and the pH adjusted from 2.78 to 13.92 with aqueous sodium hydroxide (50%, 0.3915 g, 4.90 mmol) at −4° to −2°. The mixture is warmed to 20°–25° and sonicated with stirring for 0.5 hr. Methylene chloride (55 ml), saturated aqueous sodium chloride (5 ml) and water (35 ml) is added and the phases separated. The aqueous phase is washed two times with methylene chloride (25 ml) and the combined organics dried on sodium sulfate, filtered and concentrated under reduced pressure. Toluene (5 ml) is added followed by a slow addition of heptane (25 ml). The resultant precipitate is collected by vacuum filtration, washed with heptane (20 ml) and dried to give the title compound, TLC (silica gel; methanol/chloroform 10/90) $R_f$=0.32; MS (EI), M/Z (relative intensity)=428 (28%, M$^+$), 252 (15%), 92 (32%), 91 (100%); NMR (CDCl$_3$, 300 MHz) 7.46, 7.38–7.27, 7.12, 6.90, 5.16, 4.69–4.60, 3.98, 3.80, 3.67, 3.09, 3.00–2.92 and 1.30 δ; CMR (CDCl$_3$,75 MHz) 43.94, 44.89, 47.60, 50.63, 67.23, 73.84, 107.29, 113.72, 119.37, 127.92, 128.07, 128.52, 133.79, 136.05, 136.64, 154.57, 155.19 and 155.61 δ.

Example 16

(R)-[N-3-[3-Fluoro-4-morpholinylphenyl]-2-oxo-5-oxazolidinyl]methanol 4-nitrobenzenesulfonate ester (VI)

To a slurry of (R)-[N-3-[3-fluoro-4-morpholinylphenyl]-2-oxo-5-oxazolidinyl]methanol (III, EXAMPLE 3, 43.0 g, 145 mmol) and triethylamine (36 g, 355 mmol) in methylene chloride (450 ml) at 0° is added a mixture of 4-nitrobenzenesulfonyl chloride (V, 32 g, 145 mmol) in methylene chloride (55 ml). acid (10%, 200 ml). The organic phase is separated, and the aqueous phase is The mixture is stirred in a 0° bath for 30 min and then quenched with hydrochloric extracted again with methylene chloride (200 ml). The combined organic extracts are then concentrated column chromatographed (silica gel, 4 cm×6", 40–63μ; methanol/methylene chloride 1-2/98-99, about 8 l). The appropriate fractions are combined and concentrated to give the title compound, $R_f$=0.2; NMR (CDCl$_3$, 300 MHz) 8.73, 8.54, 8.23, 7.82, 7.33, 7.04, 6.91, 4.86, 4.42, 4.12, 3.86, and 3.05 δ; CMR (CDCl$_3$, 75 MHz, partial) 46.42, 50.89, 66.87, 69.09, 69.45, 107.45, 113.95, 118.84, 123.14, 128.73, 131.08, 133.28 and 137.27 δ.

Example 17

(S)-[N-3-[3-Fluoro-4-morpholinylphenyl]-2-oxo-5-oxazolidinyl]methylamine salicylaldehyde imine A mixture of (R)-[N-3-(3-fluoro-4-(4-morpholinylphenyl)-2-oxo-5-oxazolidinyl]methanol 3-nitrobenzenesulfonate ester (VI, EXAMPLE 16, 20.608 g, 5 42.803 mmol), isopropanol (149 ml), acetonitrile (245 ml), salicylaldehyde (13.7 ml, 129 mmol) and aqueous ammonia (30%, 257 ml, 4.02 mol), is heated to 40° and stirred at 39°–42° for 24 hrs. The mixture is then cooled to −22° and the precipitate collected by vacuum filtration, washed with water (10 ml) and dried to give the title compound, TLC (silica gel; methanol/chloroform 5/95) $R_f$=0.79; EIMS (m/z, relative intensity)=399 (M$^+$, 51) 234 (11), 196 (11), 149 (22), 135 (100), 134 (47); NMR (300 MHz, CDCl$_3$) 8.44, 7.41, 7.33–6.87, 4.96–4.88, 4.12, 3.94–3.84 and 3.04 δ; CMR (CDCl$_3$, 75 MHz) 48.21, 50.99, 61.94, 66.95, 71.30, 107.68, 114.12, 117.02, 118.43, 118.82, 119.01, 131.93, 133.04, 136.51, 154.24, 155.47, 160.78 and 168.87 δ.

Example 18

(S)-[[N-3-(3-Fluoro-4-morpholinylphenyl)-2-oxo-5-oxazolidinyl]methyl]acetamide (VIII)

(S)-[N-3-[3-Fluoro-4-morpholinylphenyl]-2-oxo-5-oxazolidinyl]methylamine salicylaldehyde imine (EXAMPLE 17, 1.0068 g, 2.521 mmol) Is slurried in water (10 ml) and 37% aqueous hydrochloric acid (0.417 ml, 5.04 mmol) and stirred at 20°–25° for 15 hrs. Toluene (10 ml) is added and the phases separated; then, the organic phase is washed with hydrochloric acid (1M, 5 ml) and the combined aqueous phases are washed with toluene (10 ml). The toluene wash is back-extracted with hydrochloric acid (1M, 5 ml). The combined aqueous phases are then adjusted to pH 13.0 with aqueous sodium hydroxide (50%, 1.83 g, 22.9 mmol). To the resultant slurry is then added methylene chloride (10 ml) and sodium chloride (1 g) and the phases separated. The aqueous phase is then washed with methylene chloride (10 ml). To the combined organic phases is then added acetic anhydride (0.472 ml, 5.00 mmol) while maintaining 24°–27°. The mixture is stirred 40 min, then water is added (5 ml). The phases are separated and the aqueous phase is washed with methylene chloride (5 ml). The combined organic phases are concentrated and ethyl acetate (25 ml) is added. The mixture is warmed to 70° and then the resultant mixture is slowly cooled to −25°. The precipitate is collected by vacuum filtration, washed with −25° ethyl acetate (5 ml) and dried to give the title compound, HPLC major component (99.93 area % at 254 nm detection) retention time=0.97 min, column=Zorbax RX-C8, 250×4.6 mm, mobile phase=650 ml acetonitrile, 1.85 ml triethylamine, 1.30 ml acetic acid and sufficient water to make 1000 ml; flow rate= 3 ml/min.

Example 19

(R)-[N-3-[3-Fluoro-4-[N-1-(4-carbobenzoxy)piperazinyl]phenyl]-2-oxo-5-oxazolidinyl]methanol (III)

A mixture of N-carbobenzoxy-3-fluoro-4-(N-carbobenzoxypiperazinyl)aniline (II, 2.014 g, 4.345 mmol) and THF (10 ml) is cooled to −20°. In a separate flask, a solution of t-amyl alcohol (0.71 ml, 6.48 mmol) in THF (10 ml) at −33° is treated with n-butyllithium in heptane (13.65 wt %, 2.53 g, 5.38 mmol) while maintaining the mixture at less than −20°. The resultant lithium t-amylate solution is then added to the N-carbobenzoxy-3-fluoro-4-(N-carbobenzoxypiperazinyl)aniline mixture while maintaining less than −20° and rinsed in with THF (4 ml). To the resulting mixture at −28° is then added S-glycidol (IV, 0.3360 g, 4.536 mmol). The mixture is then stirred at −20° for 1.5 hrs, then at −16° for 17 hrs, at −11° for 4 hrs then at −1° for 2 hrs. HPLC assay then showed the major component to have a retention time consistent with the title compound (90.4 area % at 254 nm detection; retention time=1.30 min; column=Zorbax RX-C8, 250×4.6 mm; mobile phase=650 ml acetonitrile, 1.85 ml triethylamine, 1.30 ml acetic acid and add sufficient water to make 1000 ml; flow rate=3 ml/min) as did TLC (silica gel; methanol/chloroform 10/90) $R_f$=0.60.

Example 20

(R)-[N-3-[3-Fluoro-4-morpholinylphenyl]-2-oxo-5-oxazolidinyl]methanol 4-nitrobenzenesulfonate ester (VI)

Following the general procedure of EXAMPLE 16 and making non-critical variations but starting with 4-nitrobenzenesulfonyl chloride, the title compound is obtained.

Example 21

(R)-[N-3-[3-Fluoro-4-morpholinylphenyl]-2-oxo-5-oxazolidinyl]methanol 2-nitrobenzenesulfonate ester (VI)

Following the general procedure of EXAMPLE 16 and making non-critical variations but starting with 2-nitrobenzenesulfonyl chloride, the title compound is obtained.

EXAMPLE 22

(R)-[N-3-[3-Fluoro-4-morpholinylphenyl]-2-oxo-5-oxazolidinyl]methanol 2,4-dinitrobenzenesulfonate ester (VI)

Following the general procedure of EXAMPLE 16 and making non-critical variations but starting with 2,4-dinitrobenzenesulfonyl chloride, the title compound is obtained.

Example 23

(R)-[N-3-[3-Fluoro-4-morpholinylphenyl]-2-oxo-5-oxazolidinyl]methanol 4-chlorobenzenesulfonate ester (VI)

Following the general procedure of EXAMPLE 16 and making non-critical variations but starting with 4-chlorobenzenesulfonyl chloride, the title compound is obtained.

Example 24

(R)-[N-3-[3-Fluoro-4-morpholinylphenyl]-2-oxo-5-oxazolidinyl]methanol 2,5-dichlorobenzenesulfonate ester (VI)

Following the general procedure of EXAMPLE 16 and making non-critical variations but starting with 2,5-dichlorobenzenesulfonyl chloride, the title compound is obtained.

CHART A $$M_1-CH_2-CH(OH)-CH_2-OH \quad (I)$$
$$+$$
$$R_1-NH-CO-O-M_2 \quad (IIA)$$
or
$$R_1-NH-CO-CF_3 \quad (IIB)$$

↓

(III)

$$R_1\diagdown_N \diagup\!\!\!\overset{O}{\diagdown}\!\!\!\diagdown_O$$
$$\diagdown\!\!\!\diagup\cdots H$$
$$CH_2-OH$$

CHART B $$C^*H_2-C^*H-CH_2-OH \quad (IV)$$
where the carbon atoms designated by an * are each bonded to the same oxygen atom (—O—) to form a three member ring or epoxide
$$+$$
$$R_1-NH-CO-O-M_2 \quad (IIA)$$
or
$$R_1-NH-CO-CF_3 \quad (IIB)$$

CHART B -continued
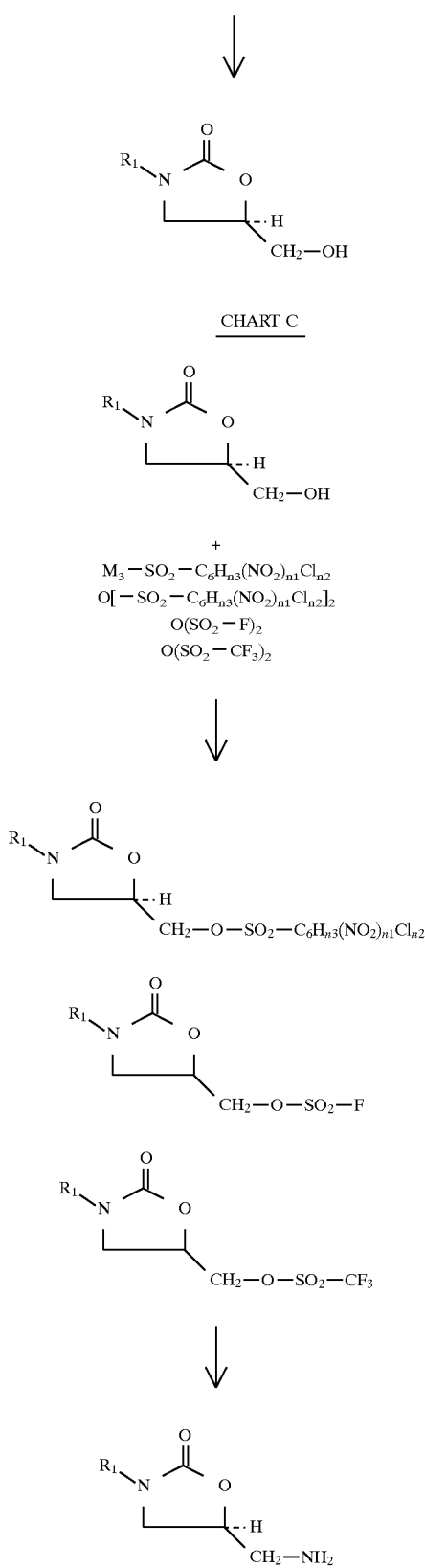
CHART D
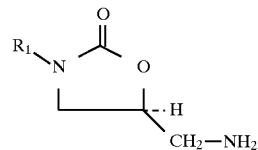
(VII)
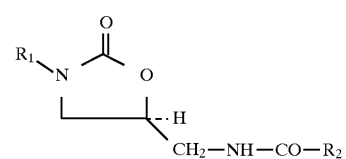
(VIII)
We claim:
1. A process to prepare 5-hydroxymethyl substituted oxazolidinones of formula (III)
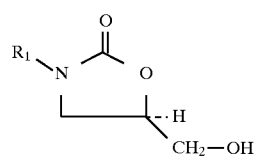
(III)
where $R_1$ is
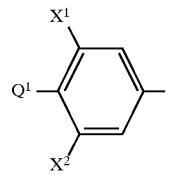
where $X^1$ is —H or —F;
where $X^2$ is —H or —F;
where $Q^1$ is:
a) 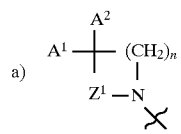
b) 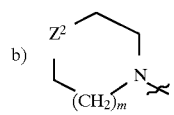
c) 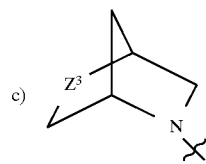
d) 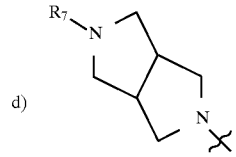

-continued f) 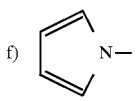

g) 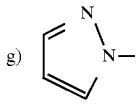

h) 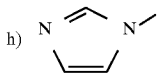

i) 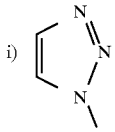

j) 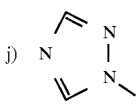

k) 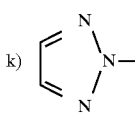

m) $R^7$—N 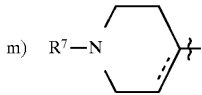

$Q^1$ and $X^2$ taken together are:

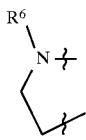

where $Z^1$ is:
a) —$CH_2$—,
b) —CH($R^4$)—$CH_2$—,
c) —C(O)—, or
d) —$CH_2CH_2CH_2$—;
where $Z^2$ is:
a) —$O_2S$—,
b) —O—,
c) —N($R^7$)—,
d) —OS—, or
e) —S—;
where $Z^3$ is:
a) —$O_2S$—,
b) —O—,
c) —OS—, or
d) —S—;
where $A^1$ is:
a) H— or
b) $CH_3$;
where $A^2$ is:
a) H—,
b) HO—,
c) $CH_3$—,
d) $CH_3O$—, e) $R^2O$—$CH_2$—C(O)—NH—
f) $R^3O$—C(O)—NH—,
g) ($C_1$-$C_2$)alkyl-O—C(O)—,
h) HO—$CH_2$—,
i) $CH_3O$—NH—,
i) ($C_1$-$C_3$)alkyl-$O_2C$—
k) $CH_3$—C(O)—,
l) $CH_3$—C(O)—$CH_2$—, m) 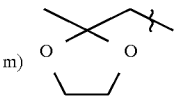

n) 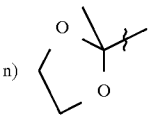

$A^1$ and $A^2$ taken together are:

a) 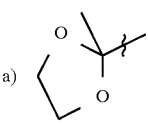

b) 

c) 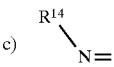

where $R^1$ is:
a) —CHO,
b) —$COCH_3$,
c) —$COCHCl_2$,
d) —$COCHF_2$,
e) —$CO_2CH_3$,
f) —$SO_2CH_3$, or
g) —$COCH_2OH$;
where $R^2$ is:
a) H—,
b) $CH_3$—,
c) phenyl-$CH_2$—, or
d) $CH_3C(O)$—;
where $R^3$ is:
a) ($C_1$-$C_3$)alkyl-, or
b) phenyl-;
where $R^4$ is:
a) H—, or
b) HO—;
where $R^5$ is:
a) H—,
b) ($C_1$-$C_3$)alkyl-,
c) $CH_2$=CH—$CH_2$— or
d) $CH_3$—O—$(CH_2)_2$—;
where $R^6$ is:
a) $CH_3$—C(O)—,
b) H—C(O)—,
c) $Cl_2CH$—C(O)—,
d) $HOCH_2$—C(O)—, e) CH$_3$SO$_2$—, f) 

g) F$_2$CHC(O)—, h) 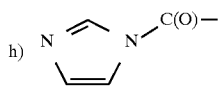

i) H$_3$C—C(O)—O—CH$_2$—C(O)—,
j) H—C(O)—O—CH$_2$—C(O)—, k) 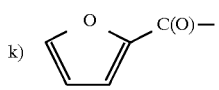

l) HC≡CH—CH$_2$O—CH$_2$—C(O)— or
m) phenyl-CH$_2$—O—CH$_2$—C(O)—;

where R$^7$ is:
 a) R$^2$O—C(R$^{10}$)(R$^{11}$)—C(O)—,
 b) R$^3$O—C(O)—,
 c) R$^8$—C(O)— d) 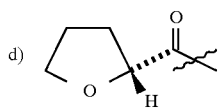

e) 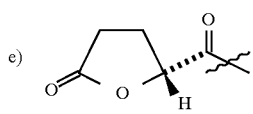

f) H$_3$C—C(O)—(CH$_2$)$_2$—C(O)—,
g) R$^9$—SO$_2$—, h) 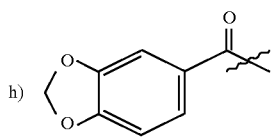

i) HO—CH$_2$—C(O)—,
j) R$^{16}$—(CH$_2$)$_2$—,
k) R$^{13}$—C(O)—O—CH$_2$—C(O)—,
l) (CH$_3$)$_2$N—CH$_2$—C(O)—NH—,
m) NC—CH$_2$— or
n) F$_2$—CH—CH$_2$—;

where R$^8$ is:
 a) H—,
 b) (C$_1$-C$_4$)alkyl,
 c) aryl —(CH$_2$)$_p$,
 d) ClH$_2$C—,
 e) Cl$_2$HC—,
 f) FH$_2$C—,
 g) F$_2$HC— or
 h) (C$_3$-C$_6$)cycloalkyl;

where R$^9$ is:
 a) —CH$_3$,
 b) —CH$_2$Cl,
 c) —CH$_2$CH=CH$_2$,
 d) aryl or e) —CH$_2$CN;

where R$^{10}$ is H— or CH$_3$—;
where R$^{11}$ is H— or CH$_3$—;
where R$^{12}$ is:
 a) H—,
 b) CH$_3$O—CH$_2$O—CH$_2$— or
 c) HOCH$_2$—;
where R$^{13}$ is:
 a) CH$_3$—,
 b) HOCH$_2$—,
 c) (CH$_3$)$_2$N-phenyl, or
 d) (CH$_3$)$_2$N—CH$_2$—;
where R$^{14}$ is:
 a) HO—,
 b) CH$_3$O—,
 c) H$_2$N—,
 d) CH$_3$O—C(O)—O—,
 e) CH$_3$—C(O)—O—CH$_2$—C(O)—O—,
 f) phenyl-CH$_2$—O—CH$_2$—C(O)—O—,
 g) HO—(CH$_2$)$_2$—O—,
 h) CH$_3$O—CH$_2$—O—(CH$_2$)$_2$—O—, or
 i) CH$_3$O—CH$_2$—O—;
where R$^{15}$ is:
 a) H— or
 b) Cl—;
where R$^{16}$ is:
 a) HO—
 b) CH$_3$O—, or
 c) F;
where m is 0 or 1;
where n is 1 thru 3;
where p is 0 or 1;
where aryl is phenyl substituted with zero (0) or one (1) of the following:
 a) —F,
 b) —Cl,
 c) —OCH$_3$,
 d) —OH,
 e) —NH$_2$,
 f) —(C$_1$-C$_4$)alkyl,
 g) —O—C(O)—OCH$_3$, or
 h) —NO$_2$ and protected forms thereof,
which comprises contacting a hydroxy compound selected from the group consisting of:
 (a) (S)-, (R)-dihydroxy compound of formula (I)

or any mixture thereof where M$_1$ is —Cl, —Br or —O—SO$_2$-φ-CH$_3$, or
 (b) (S)-, (R)- glycidol (IV)

or any mixture thereof where the carbon atoms designated by an * are each bonded to the same oxygen atom (—O—) to form a three member ring, with a carbamate of formula (IIA)

or a trifluoroacetamide of formula (IIB)

in the presence of a lithium cation and a base whose conjugate acid has a pK$_a$ of greater than about 8 where —O—$M_2$ is a base whose acid has a $pk_a$ of between about 8 and about 24, and where $R_1$ is as defined above.

2. A process to prepare 5-hydroxymethyl substituted oxazolidinones (III) according to claim 1 where the hydroxy compound is the dihydroxy compound of formula (I).

3. A process to prepare 5-hydroxymethyl substituted oxazolidinones (III) according to claim 2 where the dihydroxy compound (I) is the (S)-enantiomer.

4. A process to prepare 5-hydroxymethyl substituted oxazolidinones (III) according to claim 1 where $M_1$ is —Cl.

5. A process to prepare 5-hydroxymethyl substituted oxazolidinones (III) according to claim 4 where the dihydroxy compound (I) is (S)-(+)-3-chloro-1,2-propanediol.

6. A process to prepare 5-hydroxymethyl substituted oxazolidinones (III) according to claim 1 where the dihydroxy compound (I) is contacted with a cyclizing agent prior to be contacted with the carbamate (IIA) or trifluoroacetamide (IIB).

7. A process to prepare 5-hydroxymethyl substituted oxazolidinones (III) according to claim 6 where the cyclizing agent is a base whose acid has a $pk_a$ of greater than about 7.

8. A process to prepare 5-hydroxymethyl substituted oxazolidinones (III) according to claim 7 where the cyclizing agent is sodium, potassium or lithium butoxide, sodium or potassium hydroxide, potassium carbonate, DBU, lithium, sodium and potassium amylate.

9. A process to prepare 5-hydroxymethyl substituted oxazolidinones (III) according to claim 1 where the hydroxy compound is the glycidol (IV).

10. A process to prepare 5-hydroxymethyl substituted oxazolidinones (III) according to claim 9 where the glycidol (IV) is the (S)-enantiomer.

11. A process to prepare 5-hydroxymethyl substituted oxazolidinones (III) according to claim 1 where $M_2$ is selected from the group consisting of:

$C_1$–$C_{20}$ alkyl,
$C_3$–$C_7$ cycloalkyl,
φ- optionally substituted with one or two:
    $C_1$–$C_3$ alkyl,
    F—, Cl—, Br—, I—,
$CH_2$=CH—$CH_2$—,
$CH_3$—CH=CH—$CH_2$—,
$(CH_3)_2$C=CH—$CH_2$—,
$CH_2$=CH—,
φ-CH=CH—$CH_2$—,
φ-$CH_2$— optionally substituted on φ- with one or two —Cl, $C_1$–$C_4$ alkyl, —$NO_2$, —CN, —$CF_3$,
9-fluorenylmethyl,
$(Cl)_3$C—$CH_2$—,
2-trimethylsilylethyl,
φ-$CH_2$—$CH_2$—,
1-adamantyl,
$(φ)_2$CH—,
CH≡C—C$(CH_3)_2$—
2-furanylmethyl,
isobornyl.

12. A process to prepare 5-hydroxymethyl substituted oxazolidinones (III) according to claim 11 where $M_2$ is $C_1$–$C_4$ alkyl or benzyl.

13. A process to prepare 5-hydroxymethyl substituted oxazolidinones (III) according to claim 1 where $R_1$ is phenyl substituted with one —F and one substituted amino group.

14. A process to prepare 5-hydroxymethyl substituted oxazolidinones (III) according to claim 13 where $R_1$ is:

3-fluoro-4-[4-(benzyloxycarbonyl)-1-piperazinyl]phenyl or 3-fluoro-4-(4-morpholinyl)phenyl.

15. A process to prepare 5-hydroxymethyl substituted oxazolidinones (III) according to claim 1 where the base is selected from the group consisting of alkoxy compounds of one thru seven carbon atoms,
carbonate,
methyl, sec-butyl and t-butyl carbanions,
tri(alkyl)amines where the alkyl group is from 1 thru 4 carbon atoms,
conjugate base of the carbamate (II),
DBU,
DBN,
N-methyl-piperidine,
N-methyl morpholine and
2,2,2-trichloroethoxide.

16. A process to prepare 5-hydroxymethyl substituted oxazolidinones (III) according to claim 15 where the base is alkoxy of four or five carbon atoms.

17. A process to prepare 5-hydroxymethyl substituted oxazolidinones (III) according to claim 1 where the protected form of $R_1$ is the alcohol protecting group selected from the group consisting of:

$C_1$–$C_5$ alkyl,
φ-$CH_2$—,
$CH_3$—O—$CH_2$—,
$CH_3$—,
S—$CH_2$—,
φ-$CH_2$—O—$CH_2$—,
tetrahydropyranyl,
$CH_3$CH(—O—$C_2H_5$)—,
p-methoxybenzyl,
p-methoxyphenyl,
p-nitrobenzyl,
$(φ)_3$C—,
$(CH_3)_3$Si—,
$[CH_3$—CH$(CH_3)]_3$Si— and
φ$(CH_3)_2$Si—.

18. A process to prepare 5-hydroxymethyl substituted oxazolidinones (III) according to claim 1 where the protected form of $R_1$ is the amino protecting group selected from the group consisting of:

(I) $C_1$–$C_4$ alkyl,
(II) φ-$CH_2$—,
(III) $(φ)_3$C—,
(IV) $R_a$—CO— where $R_a$ is (A) H—, (B) $C_1$–$C_4$ alkyl, (C) $C_5$–$C_7$ cycloalkyl, (D) ($C_1$–$C_5$ alkyl)—O—, (E) $Cl_3$C—$CH_2$—O—, (F) $H_2$C=CH—$CH_2$—O—, (G) φ-CH=CH—$CH_2$—O—, (H) φ-$CH_2$—O—, (I) p-methoxyphenyl-$CH_2$—O—, (J) p-nitrophenyl-$CH_2$—O—, (K) φ-O—, (L) $CH_3$—CO—$CH_2$—, (M) $(CH_3)_3$Si—O—,
(V) $R_b$—$SO_2$— where $R_b$ is: (A) ($C_1$ alkyl)-, (B) φ-, (C) p-methylphenyl- and (D) φ-$CH_2$—.

19. A process to prepare 5-hydroxymethyl substituted oxazolidinones (III) according to claim 18 where the amino protected form of $R_1$ is benzyloxycarbonyl.

20. A process to prepare 5-aminomethyl substituted oxazolidinone amines of formula (VII)

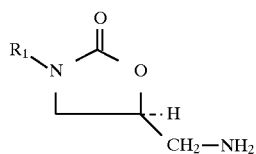

where $R_1$ is

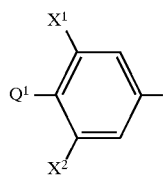

where $X^1$ is —H or —F;
where $X^2$ is —H or —F;
where $Q^1$ is:

a) 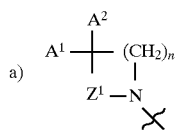

b) 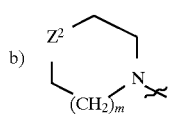

c) 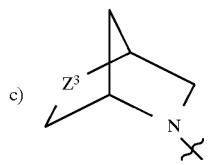

d) 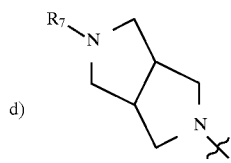

f) 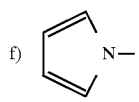

g) 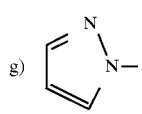

h) 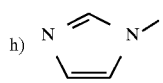

i) 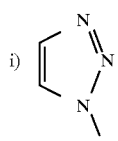

j) 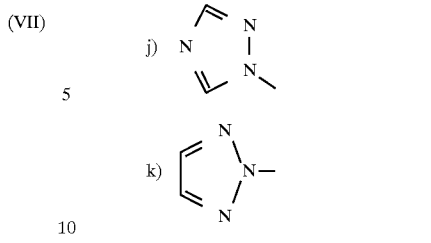

k) (shown in image above)

m) 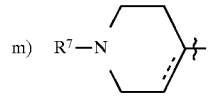

$Q^1$ and $X^2$ taken together are:

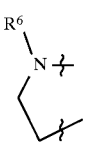

where $Z^1$ is:
  a) —CH$_2$—,
  b) —CH(R$^4$)—CH$_2$—,
  c) —C(O)—, or
  d) —CH$_2$CH$_2$CH$_2$—;
where $Z^2$ is:
  a) —O$_2$S—,
  b) —O—,
  c) —N(R$^7$)—,
  d) —OS—, or
  e) —S—;
where $Z^3$ is:
  a) —O$_2$S—,
  b) —O—,
  c) —OS—, or
  d) —S—;
where $A^1$ is:
  a) H— or
  b) CH$_3$;
where $A^2$ is:
  a) H—,
  b) HO—,
  c) CH$_3$—,
  d) CH$_3$O—,
  e) R$^2$O—CH$_2$—C(O)—NH—,
  f) R$^3$O—C(O)—NH—,
  g) (C$_1$-C$_2$)alkyl-O—C(O)—,
  h) HO—CH$_2$—,
  i) CH$_3$O—NH—,
  j) (C$_1$-C$_3$)alkyl-O$_2$C—,
  k) CH$_3$—C(O)—,
  l) CH$_3$—C(O)—CH$_2$—,
  m) 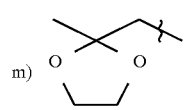

-continued n) 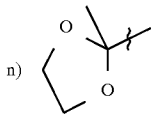

$A^1$ and $A^2$ taken together are:

a) 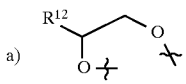

b) 

c) 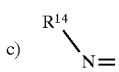

where $R^1$ is:
 a) —CHO,
 b) —COCH$_3$,
 c) —COCHCl$_2$,
 d) —COCHF$_2$,
 e) —CO$_2$CH$_3$,
 f) —SO$_2$CH$_3$, or
 g) —COCH$_2$OH;
where $R^2$ is:
 a) H—,
 b) CH$_3$—, c) phenyl-CH$_2$—, or
 d) CH$_3$C(O)—;
where $R^3$ is:
 a) (C$_1$–C$_3$)alkyl-, or
 b) phenyl-;
where $R^4$ is:
 a) H—, or
 b) HO—;
where $R^5$ is:
 a) H—,
 b) (C$_1$–C$_3$)alkyl-,
 c) CH$_2$=CH—CH$_2$— or
 d) CH$_3$—O—(CH$_2$)$_2$—;
where $R^6$ is:
 a) CH$_3$—C(O)—,
 b) H—C(O)—,
 c) Cl$_2$CH—C(O)—,
 d) HOCH$_2$—C(O)—,
 e) CH$_3$SO$_2$—, f) 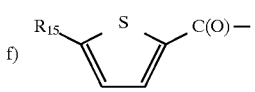

g) F$_2$CHC(O)—, h) 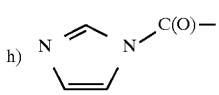

i) H$_3$C—C(O)—O—CH$_2$—C(O)—, j) H—C(O)—O—CH$_2$—C(O)—, k) 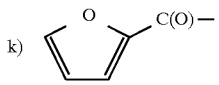

l) HC≡CH—CH$_2$O—CH$_2$—C(O)— or
m) phenyl-CH$_2$—O—CH$_2$—C(O)—;
where $R^7$ is:
 a) R$^2$O—C(R$^{10}$)(R$^{11}$)—C(O)—,
 b) R$^3$O—C(O)—,
 c) R$^8$—C(O)—, d) 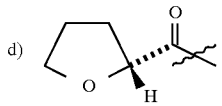

e) 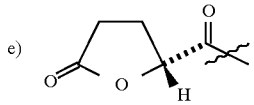

f) H$_3$C—C(O)—(CH$_2$)$_2$—C(O)—,
g) R$^9$—SO$_2$—, h) 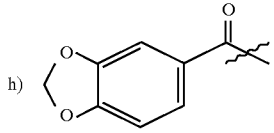

i) HO—CH$_2$—C(O)—,
j) R$^{16}$—(CH$_2$)$_2$—,
k) R$^{13}$—C(O)—O—CH$_2$—C(O)—,
l) (CH$_3$)$_2$N—CH$_2$—C(O)—NH—,
m) NC—CH$_2$— or
n) F$_2$—CH—CH$_2$—;
where $R^8$ is:
 a) H—,
 b) (C$_1$–C$_4$)alkyl,
 c) aryl —(CH$_2$)$_p$,
 d) ClH$_2$C—,
 e) Cl$_2$HC—,
 f) FH$_2$C—,
 g) F$_2$HC— or
 h) (C$_3$–C$_6$)cycloalkyl;
where $R^9$ is:
 a) —CH$_3$,
 b) —CH$_2$Cl,
 c) —CH$_2$CH=CH$_2$,
 d) aryl or
 e) —CH$_2$CN;
where $R^{10}$ is H— or CH$_3$—;
where $R^{11}$ is H— or CH$_3$—;
where $R^{12}$ is:
 a) H—,
 b) CH$_3$O—CH$_2$O—CH$_2$— or
 c) HOCH$_2$—;
where $R^{13}$ is:
 a) CH$_3$—,
 b) HOCH$_2$—,
 c) (CH$_3$)$_2$N-phenyl, or
 d) (CH$_3$)$_2$N—CH$_2$—;

where $R^{14}$ is:
a) HO—,
b) $CH_3O$—,
c) $H_2N$—,
d) $CH_3O$—C(O)—O—,
e) $CH_3$—C(O)—O—$CH_2$—C(O)—O—,
f) phenyl-$CH_2$—O—$CH_2$—C(O)—O—,
g) HO—$(CH_2)_2$—O—,
h) $CH_3O$—$CH_2$—O—$(CH_2)_2$—O—, or
i) $CH_3O$—$CH_2$—O—;

where $R^{15}$ is:
a) H— or
b) Cl—;

where $R^{16}$ is:
a) HO—
b) $CH_3O$—, or
c) F;

where m is 0 or 1;
where n is 1 thru 3;
where p is 0 or 1;
where aryl is phenyl substituted with zero (0) or one (1) of the following:
a) —F,
b) —Cl,
c) —$OCH_3$,
d) —OH,
e) —$NH_2$,
f) —$(C_1-C_4)$alkyl,
g) —O—C(O)—$OCH_3$, or
h) —$NO_2$ and protected forms thereof, which comprises:

(1) contacting 5-hydroxymethyl substituted oxazolidinone alcohols of formula (III)

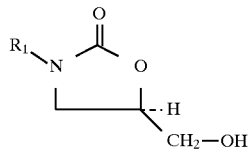

where $R_1$ is as defined above with a sulfonylating agent selected from the group consisting of compounds of formula $V_a$–$V_d$)

 ($V_a$)

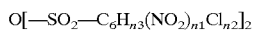 ($V_b$)

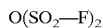 ($V_c$)

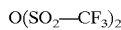 ($V_d$)

where $n_1$ is 0, 1 or 2;
where $n_2$ is 0 thru 4 with the provisos that:
if $n_1$ is 0, $n_2$ is 2, 3 or 4,
if $n_1$ is 1, $n_2$ is 0 or 1,
if $n_1$ is 2, $n_2$ is 0;
where $n_3$ is 5-$(n_1+n_2)$;
where $M_3$ is Cl— or Br— to produce the corresponding oxazolidinone sulfonate of formula ($VI_a$–$VI_d$)

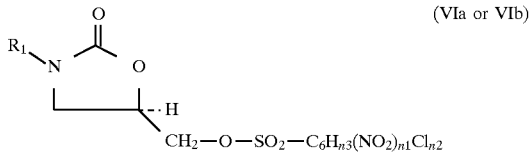 (VIa or VIb)

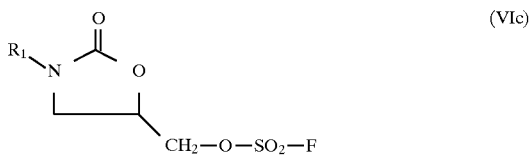 (VIc)

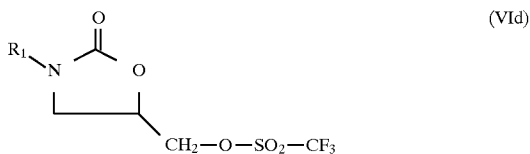 (VId)

and (2) contacting the oxazolidinone sulfonate ($VI_a$–$VI_d$) with ammonia at a pressure of less than about 30 psig.

21. A process to prepare 5-aminomethyl substituted oxazolidinone amines (VII) according to claim 20 where the sulfonylating agent (V) is selected from the group consisting of 2-nitrobenzenesulfonate, 3-nitrobenzenesulfonate, 4-nitrobenzenesulfonate, 2,4-dinitrobenzenesulfonate and 2,5-dichlorobenzenesulfonate.

22. A process to prepare 5-aminomethyl substituted oxazolidinone amines (VII) according to claim 21 where the sulfonylating agent (V) is 3-nitrobenzenesulfonate.

23. A process to prepare 5-aminomethyl substituted oxazolidinone amines (VII) according to claim 20 where step (2) is performed at about 0 to about 20 psig.

24. A process to prepare 5-aminomethyl substituted oxazolidinone amines (VII) according to claim 23 where step (2) is performed at about 0 to about 5 psig.

25. A process to prepare 5-aminomethyl substituted oxazolidinone amines (VII) according to claim 20 where step (2) is performed at about 60° or less.

26. A process to prepare 5-aminomethyl substituted oxazolidinone amines (VII) according to claim 20 where $R_1$ is phenyl substituted with one —F and one substituted amino group.

27. A process to prepare 5-aminomethyl substituted oxazolidinone amines (VII) according to claim 26 where $R_1$ is:
3-fluoro-4-[4-(benzyloxycarbonyl)-1-piperazinyl]phenyl or
3-fluoro-4-(4-morpholinyl)phenyl.

28. A process to prepare 5-aminomethyl substituted oxazolidinone amines (VII) according to claim 20 where step (2) is performed in the presence of an aromatic aldehyde.

29. A process to prepare 5-aminomethyl substituted oxazolidinone amines (VII) according to claim 28 where the aldehyde is Ar—CHO where Ar— is phenyl- optionally substituted with F—, Cl—, Br—, $C_1$-$C_5$ alkyl, HO—, $O_2N$—, $CH_3$—O— or $C_2H_5$—O—.

30. A process to prepare 5-aminomethyl substituted oxazolidinone amines (VII) according to claim 28 where the aldehyde is salicylaldehyde.

31. A process to prepare 5-aminomethyl substituted oxazolidinone amines (VII) according to claim 20 where $M_3$ is Cl—.

32. A process to prepare 5-aminomethyl substituted oxazolidinone amines (VII) according to claim 20 where step (2) is performed at atmospheric pressure.

33. A process to prepare 5-aminomethyl substituted oxazolidinone amines (VII) according to claim 20 where the contacting is performed in the presence of water.

34. A process to prepare 5-aminomethyl substituted oxazolidinone amines (VII) according to claim 20 where the sulfonylating agent (V) is $M_3$—$SO_2$—$C_6H_{n3}(NO_2)_{n1}Cl_{n2}$ ($V_a$).

35. An oxazolidinone sulfonate of formula (VIa or VIb)

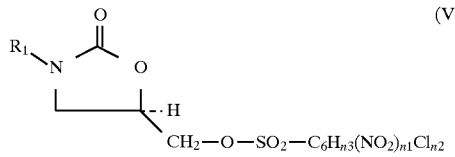

(VIa or VIb)

where $R_1$ is

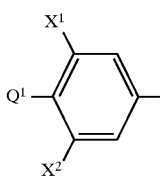

where $X^1$ is —H or —F;
where $X^2$ is —H or —F;
where $Q^1$ is:

a) 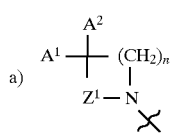

b) 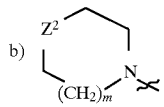

c) 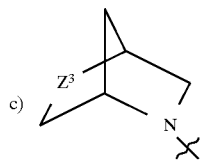

d) 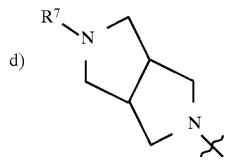

f) 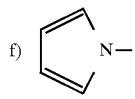

g) 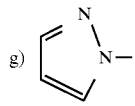

h) 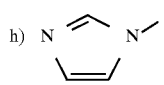

i) 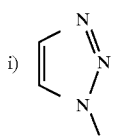

j) 

k) 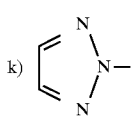

m) $R^7$—N 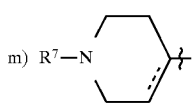

$Q^1$ and $X^2$ taken together are:

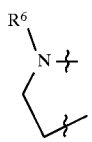

where $Z^1$ is:
a) —$CH_2$—,
b) —$CH(R^4)$—$CH_2$—,
c) —$C(O)$—, or
d) —$CH_2CH_2CH_2$—;

where $Z^2$ is:
a) —$O_2S$—,
b) —O—,
c) —$N(R^7)$—,
d) —OS—, or
e) —S—;

where $Z^3$ is:
a) —$O_2S$—,
b) —O—,
c) —OS—, or
d) —S—;

where $A^1$ is:
a) H— or
b) $CH_3$;

where $A^2$ is:
a) H—,
b) HO—,
c) $CH_3$—,
d) $CH_3O$—,
e) $R^2O$—$CH_2$—$C(O)$—NH—
f) $R^3O$—$C(O)$—NH—,
g) ($C_1$-$C_2$)alkyl -O—$C(O)$—,
h) HO—$CH_2$—,
i) $CH_3O$—NH—,
j) ($C_1$-$C_3$)alkyl-$O_2C$—
k) $CH_3$—$C(O)$—, l) CH₃—C(O)—CH₂—, m) 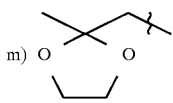

n) 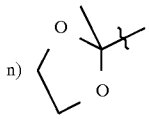

A¹ and A² taken together are:

a) 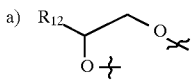

b) O= c) 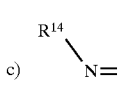

where R¹ is:
a) —CHO,
b) —COCH₃,
c) —COCHCl₂,
d) —COCHF₂,
e) —CO₂CH₃,
f) —SO₂CH₃, or
g) —COCH₂OH;

where R² is:
a) H—,
b) CH₃—,
c) phenyl-CH₂—, or
d) CH₃C(O)—;

where R³ is:
a) (C₁-C₃)alkyl-, or
b) phenyl-;

where R⁴ is:
a) H—, or
b) HO—;

where R⁵ is:
a) H—,
b) (C₁-C₃)alkyl-,
c) CH₂=CH—CH₂— or
d) CH₃—O—(CH₂)₂—;

where R⁶ is:
a) CH₃—C(O)—,
b) H—C(O)—,
c) Cl₂CH—C(O)—,
d) HOCH₂—C(O)—,
e) CH₃SO₂—, f) 

g) F₂CHC(O)—, h) 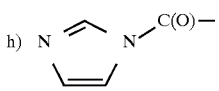

i) H₃C—C(O)—O—CH₂—C(O)—, j) H—C(O)—O—CH₂—C(O)—, k) 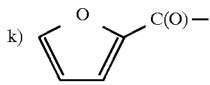

l) HC≡CH—CH₂O—CH₂—C(O)— or
m) phenyl-CH₂—O—CH₂—C(O)—;

where R⁷ is:
a) R²O—C(R¹⁰)(R¹¹)—C(O)—,
b) R³O—C(O)—,
c) R⁸—C(O)—, d) 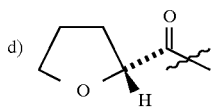

e) 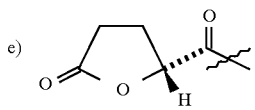

f) H₃C—C(O)—(CH₂)₂—C(O)—,
g) R⁹—SO₂—, h) 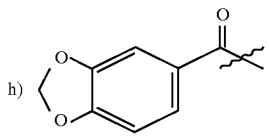

i) HO—CH₂—C(O)—,
j) R¹⁶—(CH₂)₂—,
k) R¹³—C(O)—O—CH₂—C(O)—,
l) (CH₃)₂N—CH₂—C(O)—NH—,
m) NC—CH₂— or
n) F₂—CH—CH₂—;

where R⁸ is:
a) H—,
b) (C₁-C₄)alkyl,
c) aryl —(CH₂)ₚ,
d) ClH₂C—,
e) Cl₂HC—,
f) FH₂C—,
g) F₂HC— or
h) (C₃-C₆)cycloalkyl;

where R⁹ is:
a) —CH₃,
b) —CH₂Cl,
c) —CH₂CH=CH₂,
d) aryl or
e) —CH₂CN;

where R¹⁰ is H— or CH₃—;
where R¹¹ is H— or CH₃—;
where R¹² is:
a) H—,
b) CH₃O—CH₂O—CH₂— or
c) HOCH₂—;

where R¹³ is:
a) CH₃—,
b) HOCH₂—,
c) (CH₃)₂N-phenyl, or
d) (CH₃)₂N—CH₂—;

where $R^{14}$ is:
a) HO—,
b) $CH_3O$—,
c) $H_2N$—,
d) $CH_3O$—C(O)—O—,
e) $CH_3$—C(O)—O—$CH_2$—C(O)—O—,
f) phenyl-$CH_2$—O—$CH_2$—C(O)—O—,
g) HO—$(CH_2)_2$—O—,
h) $CH_3O$—$CH_2$—O—$(CH_2)_2$—O—, or
i) $CH_3O$—$CH_2$—O—;
where $R^{15}$ is:
a) H— or
b) Cl—;
where $R^{16}$ is:
a) HO—
b) $CH_3$—, or
c) F;
where m is 0 or 1;
where n is 1 thru 3;
where p is 0 or 1;
where aryl is phenyl substituted with zero (0) or one (1) of the following:
a) —F,
b) —Cl,
c) —$OCH_3$,
d) —OH,
e) —$NH_2$,
f) —$(C_1-C_4)$alkyl,
g) —O—C(O)—$OCH_3$, or
h) —$NO_2$ and protected forms thereof,
where $n_1$ is 0, 1 or 2;
where $n_2$ is 0 thru 4 with the provisos that:
if $n_1$ is 0, $n_2$ is 2,3 or 4,
if $n_1$ is 1, $n_2$ is 0 or 1,
if $n_1$ is 2, $n_2$ is 0;
where $n_3$ is 5-$(n_1+n_2)$.

36. An oxazolidinone sulfonate (VIa or VIb) according to claim 35 which is:

3-nitrobenzenesulfonate ester (R)-[N-3-[3-fluoro-4-(N-1-(4-carbobenzoxy) piperazinyl]-phenyl]-2-oxo-5-oxazolidinyl]methanol, 2-nitrobenzenesulfonate ester (R)-[N-3-[3-fluoro-4-[N-1-(4-carbobenzoxy) piperazinyl]phenyl]-2-oxo-5-oxazolidinyl]methanol, 2,4-dinitrobenzenesulfonate ester (R)-[N-3-[3-fluoro-4-[N-1-(4-carbobenzoxy) piperazinyl]phenyl]-2-oxo-5-oxazolidinyl]methanol, (R)-[N-3-[3-fluoro-4-[N-1(4-carbobenzoxy)piperazinyl] phenyl]-2-oxo-5-oxazolidinyl]methanol 4-chlorobenzenesulfonate ester, (R)-[N-3-[3-fluoro-4-[N-1(4-carbobenzoxy)piperazinyl] phenyl]-2-oxo-5-oxazolidinyl]methanol 2,5-dichlorobenzenesulfonate ester, (R)-[N-3-[3-fluoro-4-[N-1(4-carbobenzoxy)piperazinyl] phenyl]-2-oxo-5-oxazolidinyl]methanol 4-nitrobenzenesulfonate ester, (R)-[N-3-[3-fluoro-4-morpholinylphenyl]-2-oxo-5-oxazolidinyl]methanol 3-nitrobenzenesulfonate ester, (R)-[N-3-[3-fluoro-4-morpholinylphenyl]-2-oxo-5-oxazolidinyl]methanol 4-nitrobenzenesulfonate ester, (R)-[N-3-[3-fluoro-4-morpholinylphenyl]-2-oxo-5-oxazolidinyl]methanol 2-nitrobenzenesulfonate ester, (R)-[N-3-[3-fluoro-4-morpholinylphenyl]-2-oxo-5-oxazolidinyl]methanol 2,4-dinitrobenzenesulfonate ester, (R)-[N-3-[3-fluoro-4-morpholinylphenyl]-2-oxo-5-oxazolidinyl]methanol 4-chlorobenzenesulfonate ester, (R)-[N-3-[3-fluoro-4-morpholinylphenyl]-2-oxo-5-oxazolidinyl]methanol 2,5-dichlorobenzenesulfonate ester.

37. An oxazolidinone sulfonate (VIa or VIb) according to claim 36 which is:

3-nitrobenzenesulfonate ester (R)-[N-3-[3-fluoro-4-(N-1-(4-carbobenzoxy)piperazinyl]-phenyl]-2-oxo-5-oxazolidinyl]methanol, 2-nitrobenzenesulfonate ester (R)-[N-3-[3-fluoro-4-[N-1-(4-carbobenzoxy)piperazinyl]phenyl]-2-oxo-5-oxazolidinyl]methanol, 2,4-dinitrobenzenesulfonate ester (R)-[N-3-[3-fluoro-4-[N-1-(4-carbobenzoxy)piperazinyl]phenyl]-2-oxo-5-oxazolidinyl]methanol, (R)-[N-3-[3-fluoro-4-[N-1-(4-carbobenzoxy)piperazinyl] phenyl]-2-oxo-5-oxazolidinyl]methanol 4-chlorobenzenesulfonate ester, (R)-[N-3-[3-fluoro-4-[N-1-(4-carbobenzoxy)piperazinyl] phenyl]-2-oxo-5-oxazolidinyl]methanol 2,5-dichlorobenzenesulfonate ester, (R)-[N-3-[3-fluoro-4-[N-1-(4-carbobenzoxy)piperazinyl] phenyl]-2-oxo-5-oxazolidinyl]methanol 4-nitrobenzenesulfonate ester, (R)-[N-3-[3-fluoro-4-morpholinylphenyl]-2-oxo-5-oxazolidinyl]methanol 3-nitrobenzenesulfonate ester.

* * * * *

UNITED STATES PATENT AND TRADEMARK OFFICE
CERTIFICATE OF CORRECTION

PATENT NO. : 5,837,870
DATED : November 17, 1998
INVENTOR(S) : BA Pearlman et al.

It is certified that error appears in the above-identified patent and that said Letters Patent is hereby corrected as shown below:

Column 24,
Lines 28 and 34, change "4-nitro..." to -- 3-nitro... --

Signed and Sealed this

Nineteenth Day of February, 2002

Attest:

Attesting Officer

JAMES E. ROGAN
*Director of the United States Patent and Trademark Office*